(12) United States Patent
Fedurco

(10) Patent No.: US 9,035,013 B2
(45) Date of Patent: May 19, 2015

(54) SULPHUR-CONTAINING TRIAZINE MONOMER THAT CAN BE USED FOR THE SYNTHESIS OF A POLYMER MEMBRANE FOR A FUEL CELL

(75) Inventor: Milan Fedurco, Clermont-Ferrand (FR)

(73) Assignees: COMPAGNIE GENERALE DES ETABLISSEMENTS MICHELIN, Clermont-Ferrand (FR); MICHELIN RECHERCHE ET TECHNIQUE S.A., Granges-Paccot (CH)

( * ) Notice: Subject to any disclaimer, the term of this patent is extended or adjusted under 35 U.S.C. 154(b) by 285 days.

(21) Appl. No.: 13/812,887

(22) PCT Filed: Jul. 6, 2011

(86) PCT No.: PCT/EP2011/061424
§ 371 (c)(1),
(2), (4) Date: Mar. 25, 2013

(87) PCT Pub. No.: WO2012/016778
PCT Pub. Date: Feb. 9, 2012

(65) Prior Publication Data
US 2013/0184428 A1      Jul. 18, 2013

(30) Foreign Application Priority Data
Aug. 4, 2010   (FR) .................... 10 56438

(51) Int. Cl.
| | | |
|---|---|---|
| *C08G 75/00* | (2006.01) | |
| *C07D 251/24* | (2006.01) | |
| *B01D 67/00* | (2006.01) | |
| *B01D 71/32* | (2006.01) | |
| *B01D 71/62* | (2006.01) | |
| *B01D 71/66* | (2006.01) | |
| *B01D 71/68* | (2006.01) | |
| *B01D 71/82* | (2006.01) | |
| *C08G 73/06* | (2006.01) | |
| *C08J 5/22* | (2006.01) | |
| *H01M 8/10* | (2006.01) | |

(52) U.S. Cl.
CPC .......... *C07D 251/24* (2013.01); *B01D 67/0009* (2013.01); *B01D 71/32* (2013.01); *B01D 71/62* (2013.01); *B01D 71/66* (2013.01); *B01D 71/68* (2013.01); *B01D 71/82* (2013.01); *C08G 73/0638* (2013.01); *C08G 73/0644* (2013.01); *C08J 5/2262* (2013.01); *C08J 2381/06* (2013.01); *H01M 8/1027* (2013.01); *H01M 8/103* (2013.01); *H01M 8/1032* (2013.01); *H01M 8/1039* (2013.01); *H01M 2008/1095* (2013.01); *H01M 2300/0082* (2013.01); *Y02E 60/521* (2013.01); *B01D 2325/14* (2013.01); *B01D 2325/26* (2013.01); *B01D 2325/30* (2013.01)

(58) Field of Classification Search
USPC .......................... 528/172, 125, 86, 168, 211
See application file for complete search history.

(56) References Cited

U.S. PATENT DOCUMENTS

| | | | |
|---|---|---|---|
| 6,495,209 | B1 | 12/2002 | Cisar ............................. 427/384 |
| 7,037,614 | B1 | 5/2006 | Cooray et al. .................. 429/33 |
| 7,901,821 | B2 | 3/2011 | Buchi et al. .................... 429/429 |
| 2004/0236062 | A1 | 11/2004 | Hofmann ....................... 528/125 |
| 2005/0221135 | A1 | 10/2005 | Cooray et al. .................. 429/20 |
| 2008/0160363 | A1 | 7/2008 | Tsukada ........................ 429/19 |
| 2010/0040930 | A1 | 2/2010 | Delfino et al. ................. 429/34 |

(Continued)

FOREIGN PATENT DOCUMENTS

| | | |
|---|---|---|
| JP | 2001-277720 A | 10/2001 |
| WO | WO 2005/006472 A1 | 1/2005 |

(Continued)

OTHER PUBLICATIONS

L.V. Johnson, et al., "Organic Fluorides. Part XIV. The Synthesis of Some Aromatic Fluoro-and Chloro-compounds", J. Chem. Soc., pp. 4710-4713 (1952).
Office Action in U.S. Appl. No. 13/812,885 (now U.S. Patent No. 8,889,817) dated Feb. 28, 2014.
D.M. Tigelaar et al., "Synthesis and Properties of Novel Proton-Conducting Aromatic Poly(ether sulfone)s That Contain Triazine Groups," Macromolecules, vol. 42, pp. 1888-1896 (2009).

(Continued)

*Primary Examiner* — Shane Fang
(74) *Attorney, Agent, or Firm* — Fitzpatrick, Cella, Harper & Scinto

(57) ABSTRACT

A sulphur-containing triazine monomer is provided that can be used in the synthesis of a polymer membrane for a PEM-type fuel cell. The sulphur-containing triazine monomer has a structure corresponding to a formula (I):

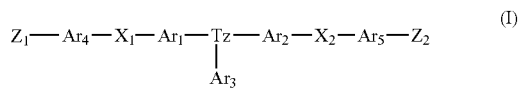

Figure 1A:
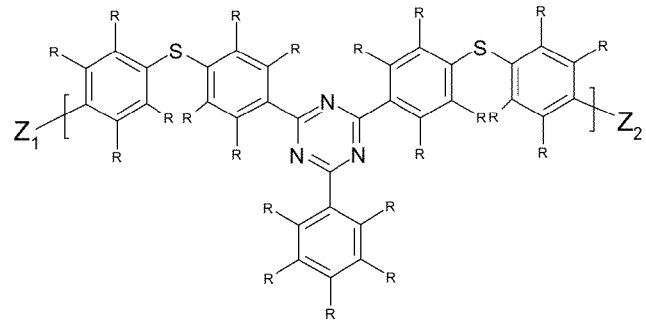

in which:
   Tz represents a 1,3,5-triazine nucleus;
   $X_1$ and $X_2$, which are identical or different, represent S, SO, or $SO_2$;
   $Ar_1$, $Ar_2$, $Ar_4$ and $Ar_5$, which are identical or different, represent a substituted or unsubstituted phenylene group;
   $Ar_3$ represents a substituted or unsubstituted phenyl group; and
   $Z_1$ and $Z_2$, which are identical or different, are selected from a group that includes halogens, hydroxyl, alkoxyl, thiol, carboxyl, carboxylates, amine, sulphonamide, acyl chlorides, sulphonyl chlorides, sulphonyl fluorides, isocyanates, and combinations thereof.

10 Claims, 24 Drawing Sheets

(56) References Cited

U.S. PATENT DOCUMENTS

2010/0173227 A1  7/2010  Olsommer .................. 429/514
2011/0311899 A1  12/2011 Onodera et al. ............. 429/482

FOREIGN PATENT DOCUMENTS

| WO | WO 2006/012953 A2 | 2/2006 |
| WO | WO 2006/012954 A1 | 2/2006 |
| WO | WO 2006/100029 A1 | 9/2006 |
| WO | WO 2008/125174 A1 | 10/2008 |
| WO | 2012/016779 A1 | 2/2012 |
| WO | 2012/016780 A1 | 2/2012 |

OTHER PUBLICATIONS

R. Souzy et al., "Functional fluoropolymers for fuel cell membranes," Progress in Polymer Science, vol. 30 (2005), pp. 644-687.

R.D. Spencer et al., "Determination of Four Closely Related Triaryl-s-Triazines by Infrared Spectrometry," Analytical Chemistry, vol. 35, No. 11 (Oct. 1963), pp. 1633-1636.

A.E. Feiring et al., "Fluorinated Poly(ether Sulfone)s," Journal of Polymer Science: Part A: Polymer Chemistry, vol. 28 (1990), pp. 2809-2819.

X. Zhu et al., "Challenging reinforced composite polymer electrolyte membranes based on disulfonated poly(arylene ether sulfone)-impregnated expanded PTFE for fuel cell applications," Journal of Material Chemistry, vol. 17 (2007), pp. 386-397.

(I-1)

(I-2)

(I-3)

(II-1)

(II-2)

(II-3)

(II-1-A)

(II-2-A)

(II-3-A)

(II-1-B)

(II-2-B)

(II-3-B)

(III-1)

(III-2)

(III-3)

(III-1-A)

(III-2-A)

(III-3-A)

(III-1-B)

(III-2-B)

(III-3-B)

Monomer A5     Monomer B5

Base,
organic solvent
(Δ)

Polymer 5

Compound 1

Compound 1  Compound 2

Compound 2  Compound 3

Compound 7

Compound 8

Compound 8 Compound 9

Polymer 7

Fig. 23
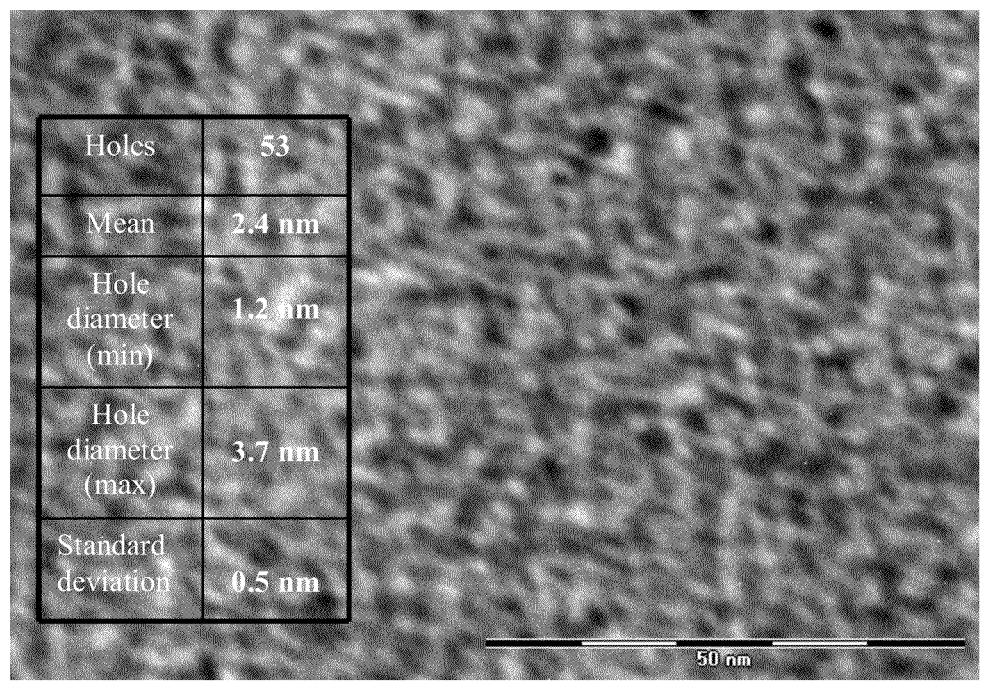
Fig. 23A
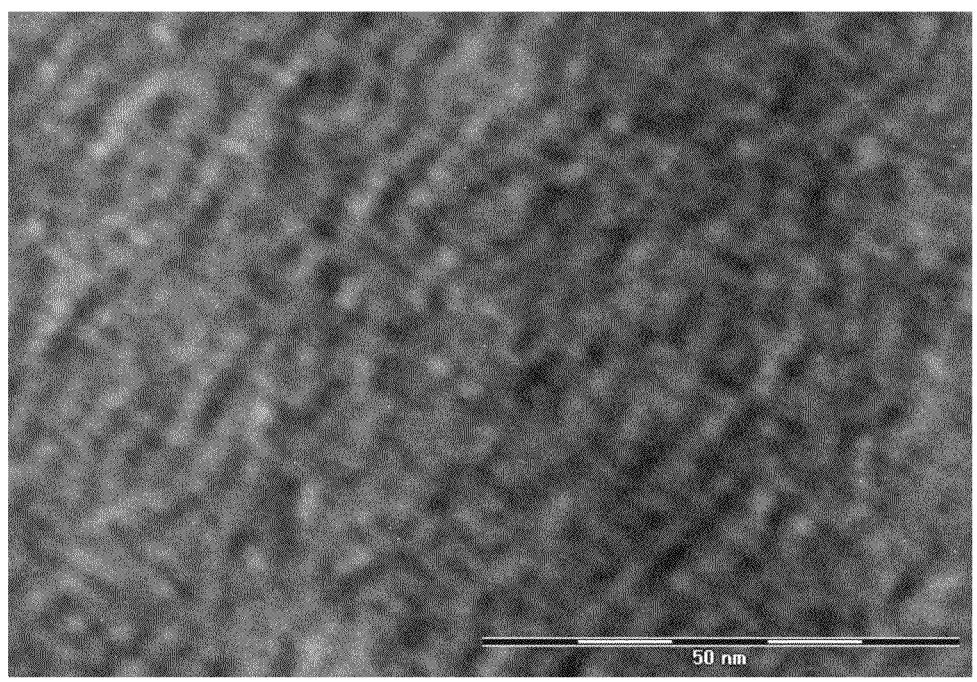
Fig. 23B

SULPHUR-CONTAINING TRIAZINE MONOMER THAT CAN BE USED FOR THE SYNTHESIS OF A POLYMER MEMBRANE FOR A FUEL CELL

I. FIELD OF THE INVENTION

The present invention relates to the monomers which can be used for the synthesis of polymers intended in particular, in the sulphonated form, to constitute a solid electrolyte or membrane in a fuel cell.

It relates more particularly to the above monomers of the aromatic type comprising a base structural unit with a triazine nucleus.

II. STATE OF THE ART

The recent interest in fuel cells arises from their ability to convert chemical energy into electricity with a relatively high yield and a low emission of environmental pollutants. The use of such electrochemical devices extends today from the motor vehicle industry to portable computers, to mobile phones, to the stationary generation of electrical energy and to other applications comprising exploration of the sea and space.

It should be remembered first of all that a fuel cell is an electrochemical energy generator in which a chemical reaction between hydrogen and oxygen is maintained under control, which reaction will produce water (reverse reaction to electrolysis). It produces electrical energy and heat. The electrolyte therein is typically composed of a PEM (Polymer Electrolyte Membrane) which conducts protons and which is capable of separating the reactive entities, consisting of two very distinct nanophases: on the one hand, a hydrophobic part which provides mechanical integrity, watertightness and gastightness (the gases being $H_2$ and $O_2$) and, on the other hand, a sulphonated part consisting of narrow hydrophilic channels allowing the protons to pass and thus providing the ionic conductivity of the cell. This polymer membrane is positioned between the anode and the cathode of the cell, such an assembly being commonly referred to as "MEA" (Membrane Electrode Assembly).

Such fuel cells, MEA assemblies and their general operating principles are well known. They have been described in a very large number of documents; mention may be made, as examples, of the general article entitled "*Functional fluoropolymers for fuel cell membranes*" by Renaud Souzy & Bruno Ameduri, Prog. Polymer Sci., 30 (2005), 644-687, and Patent Applications WO 2005/006472, WO 2006/012953, WO 2006/012954, WO 2006/100029 and WO 2008/125174.

A polymeric material which is a good candidate for a PEM fuel cell must meet very high requirements as regards its mechanical, physical and chemical properties. Ideally, the MEA assembly is expected to be able to operate for thousands of hours at relatively high temperatures (60 to 100° C. in the case of PEM cells, up to 160° C. in the case of methanol cells referred to as DMFCs) while being exposed to particularly high humidity and acidic pH values close to zero. The majority of known polymers undergo decomposition under such conditions, whether of aliphatic type or of aromatic type.

Aliphatic copolymers derived from perfluorosulphonic acid, sold, for example, under the Nafion® or Flemion® name, have been intensively employed as conducting membranes in fuel cells of the hydrogen/air, hydrogen/oxygen or methanol/air type.

Despite a very good ion conductivity and a high chemical stability, the use of polymers of the Nafion® type is first of all not suited to employment in fuel cells of the methanol type, due to reduced performance for the highest operating temperatures, due to a significant increase in permeability of the membrane with regard to the methanol.

Another known disadvantage of the polymers of the Nafion® type, in operation in the cell, is their relatively limited chemical stability. This is because perfluoropolymers are known to absorb large amounts of water responsible for repeated dimensional changes and swellings of the membrane: repeated cycles of drying and humidification, during successive shutdowns and startups of the fuel cell, result in an increased permeability to gases ($H_2$ and $O_2$); this increased permeability is responsible for the formation of hydrogen peroxide and free radicals (OH), so many mechanisms which can result in rapid degradation in a membrane and in the premature end of life of the fuel cell. In order to limit these dimensional changes and to thus improve the endurance of the membranes, it has been proposed in particular to add, as reinforcing polymer, a second fluoropolymer, in particular a PTFE (polytetrafluoroethylene) of the expanded microporous (or "ePTFE") type, and to thus form tougher composite membranes (see, for example, U.S. Pat. No. 6,495,209).

Finally, another major disadvantage of the polymers of the Nafion® type is the cost of their synthesis, without mentioning a base chemistry which no longer corresponds today to the most recent requirements in terms of the environment and of health and safety regulations.

Consequently, much research has been carried out in the past in an attempt to reduce the cost of the PEM membranes.

It has in particular been proposed to replace the above aliphatic polymers with aromatic polymers, which are lower in cost and which furthermore have the advantage of exhibiting a reduced permeability to the gases ($H_2$ and $O_2$).

Examples of such polymers are, for example, poly(arylene-ether-sulphone)s, sold in particular under the "Udel" or "Radel" names, or poly(ether-ether-ketone)s, sold, for example, under the "PEEK" name. The above aromatic polymers, once sulphonated, still do not make it possible today to achieve the compromise in performance and in cost offered with the fluorinated aliphatic polymers of the Nafion® type. In addition, these aromatic polymers generally mix poorly with an ePTFE-type polymer and the membranes which result therefrom thus cannot be easily reinforced with an ePTFE polymer, such a reinforcing requiring a preliminary surface treatment of the ePTFE polymer by plasma or by the chemical route in very aggressive chemical media (see, for example, the paper entitled "*Challenging reinforced composite polymer electrolyte membranes based on disulfonated poly(arylene-ether-sulfone)-impregnated expanded PTFE for fuel cell applications*", Xiaobing Zhu et al., J. Mat. Chem., 2007, 386-397).

Other examples of polymers of the aromatic type have been described more recently in the patent documents US2005/0221135 and U.S. Pat. No. 7,037,614. They are sulphonated triazine polymers, the monomers of which are connected via ether (—O—) bridges. The syntheses described in these documents are complex, expensive and difficult to reproduce. In addition, it has been found that their chemical and dimensional stability is insufficient even after a final crosslinking treatment of the membranes, which treatment furthermore requires another complex and expensive chemistry.

III. BRIEF DESCRIPTION OF THE INVENTION

During their research studies, the Applicant Companies have found a novel aromatic monomer, more specifically a monomer comprising a specific triazine nucleus, which can be used for the synthesis of a polymer membrane making it possible to overcome, at least in part, the abovementioned disadvantages.

This triazine monomer of the invention is a sulphur-containing triazine monomer corresponding to the formula:

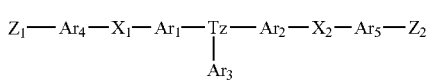

in which:
- the symbol Tz represents the 1,3,5-triazine nucleus;
- the symbols $X_1$ and $X_2$, which are identical or different, represent S, SO or $SO_2$;
- the symbols $Ar_1$, $Ar_2$, $Ar_4$ and $Ar_5$, which are identical or different, represent a substituted or unsubstituted phenylene group;
- the symbol $Ar_3$ represents a substituted or unsubstituted phenyl group;
- the symbols $Z_1$ and $Z_2$, which are identical or different, are selected from the group consisting of halogens, hydroxyl, alkoxyls, thiol, carboxyls, carboxylates, amino, sulphonamido, acyl chloride, sulphonyl chloride, sulphonyl fluoride, isocyanate and their mixtures.

By virtue of this triazine monomer in accordance with the invention, it is possible to prepare a triazine polymer which, in comparison with the triazine polymers of the prior art described above, has a markedly improved chemical stability and a markedly improved resistance to oxidation. It makes it possible to manufacture PEM membranes which, unexpectedly, in comparison with commercial membranes of the Nafion® type developed a long time ago, exhibit a chemical and dimensional stability and an ion conductivity which are at least equivalent, if not superior. Finally, the triazine polymer resulting from the monomer of the invention can, which is not the least of its advantages, be rendered compatible with a microporous ePTFE polymer for optimal reinforcing of the membrane, without requiring the surface treatments which were mentioned above.

The invention also relates to a process for the synthesis of a triazine polymer by polycondensation of at least one triazine monomer in accordance with the invention.

The invention also relates to the use of a triazine monomer in accordance with the invention for the manufacture of a polymer membrane which can be used in a fuel cell of the PEM type.

Figure 7A:
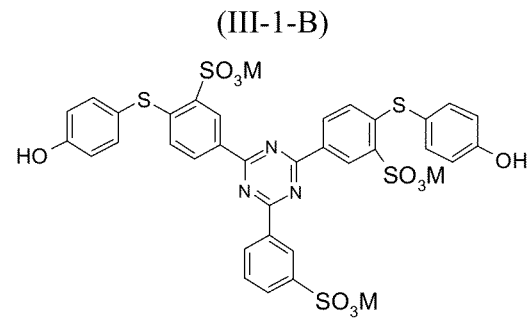
Figure 7B:
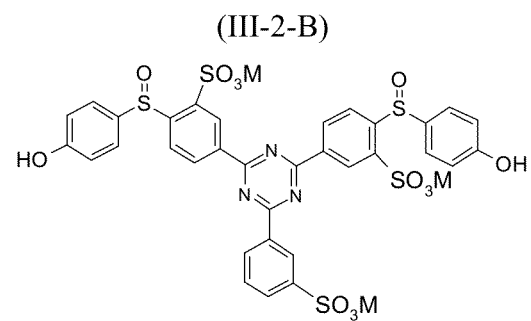
Figure 7C:
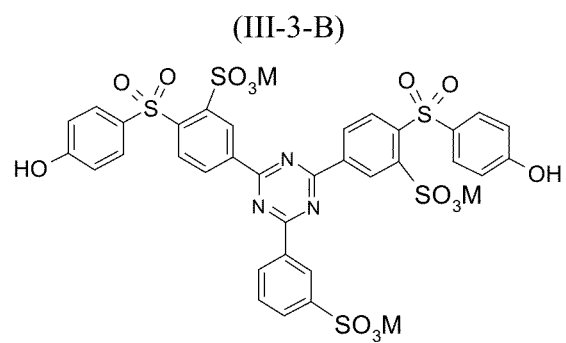
Figure 8:
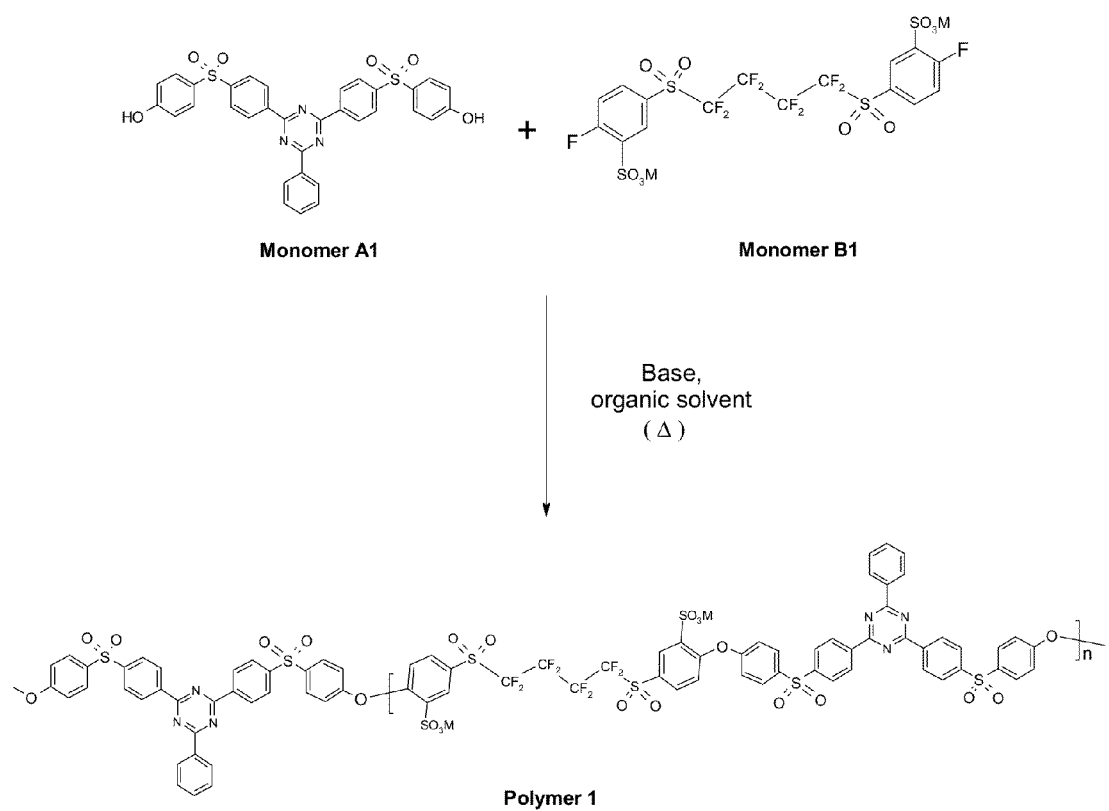
Figure 13:
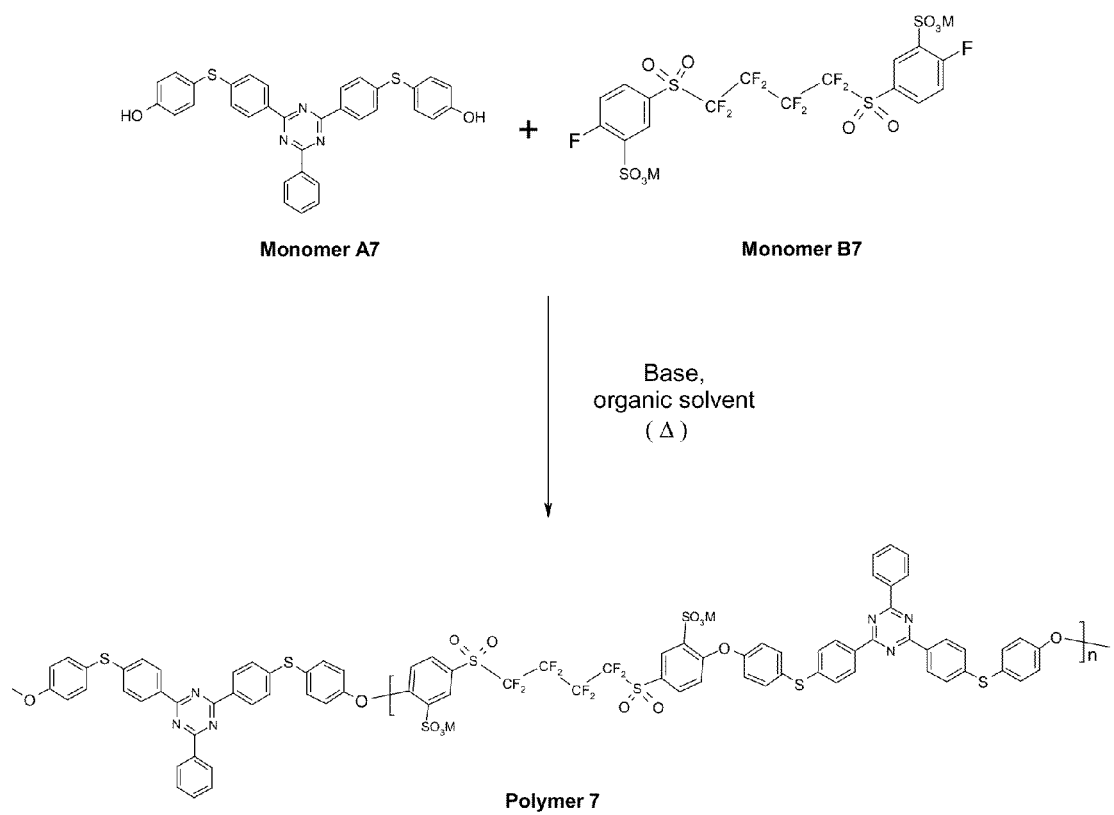
Figure 14:
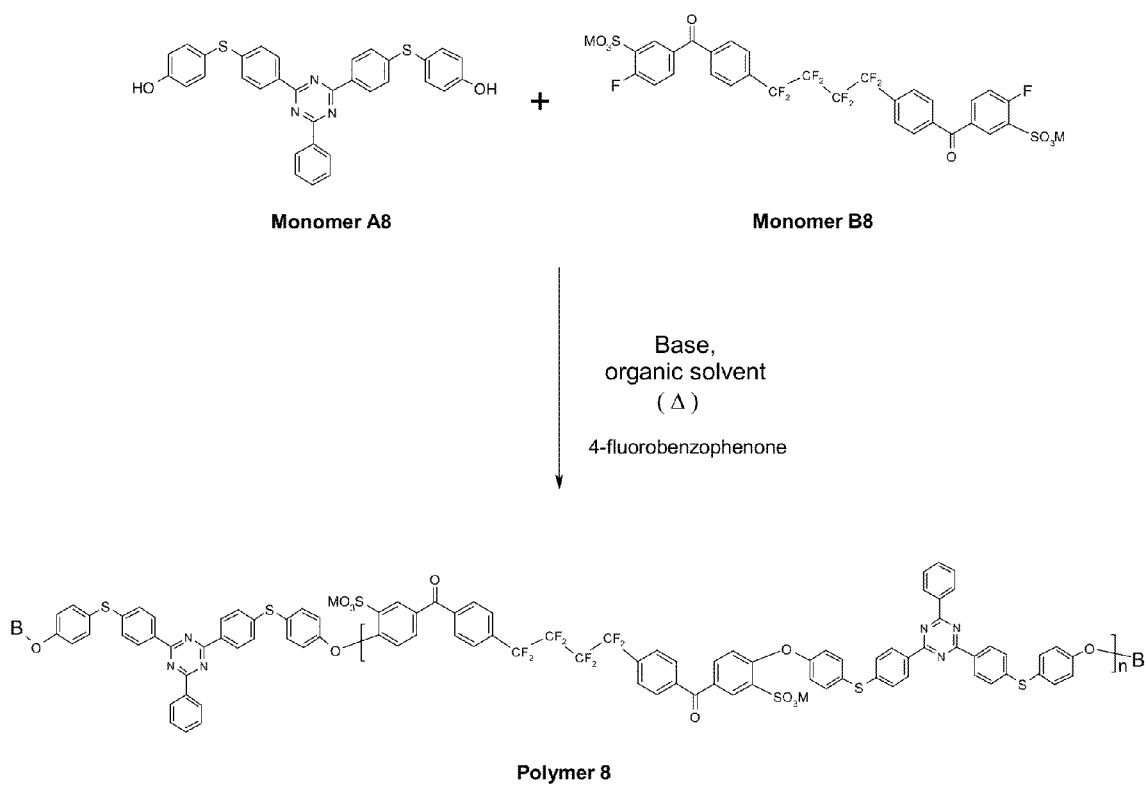
Figure 24:
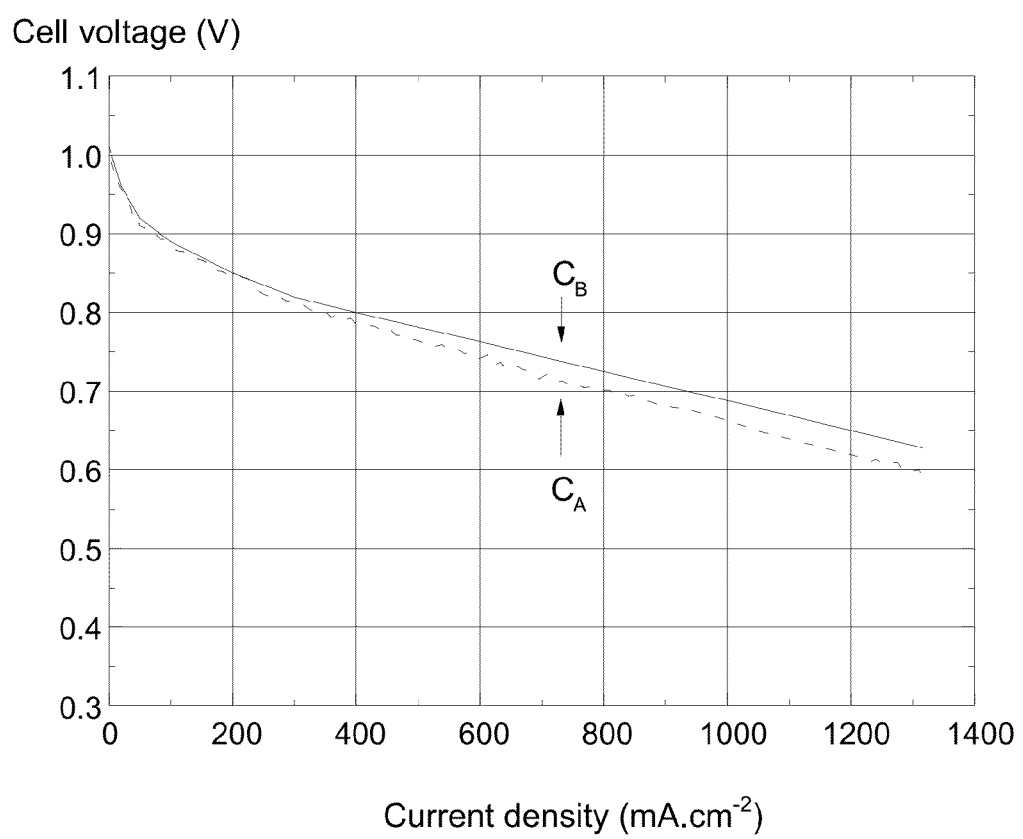

The invention and its advantages will be easily understood in the light of the detailed description and implementational examples which follow, and also of the figures relating to these examples, which represent or schematize:
- examples of monomers in accordance with the invention of formula (I), of respective specific formulae (I-1), (I-2) and (I-3) (FIGS. 1A, 1B and 1C);
- examples of monomers in accordance with the invention of formula (II), of respective specific formulae (II-1), (II-2) and (II-3) (FIGS. 2A, 2B and 2C);
- examples of monomers in accordance with the invention of formula (II), of respective specific formulae (II-1-A), (II-2-A) and (II-3-A) (FIGS. 3A, 3B and 3C);
- examples of monomers in accordance with the invention of formula (II), of respective specific formulae (II-1-B), (II-2-B) and (II-3-B) (FIGS. 4A, 4B and 4C);
- examples of monomers in accordance with the invention of formula (III), of respective specific formulae (III-1), (III-2) and (III-3) (FIGS. 5A, 5B and 5C);
- examples of monomers in accordance with the invention of formula (III), of respective specific formulae (III-1-A), (III-2-A) and (III-3-A) (FIGS. 6A, 6B and 6C);
- examples of monomers in accordance with the invention of formula (III), of respective specific formulae (III-1-B), (III-2-B) and (III-3-B) (FIGS. 7A, 7B and 7C);
- an example of a triazine polymer (Polymer 1) and also a possible scheme for the synthesis of this polymer by polycondensation of a monomer A1 in accordance with the invention with a second monomer B1 not in accordance with the invention (FIG. 8);
- another example of a triazine polymer (Polymer 2) and also a possible scheme for the synthesis of this polymer by polycondensation of a monomer A2 in accordance with the invention with a second monomer B2 not in accordance with the invention (FIG. 9);
- another example of a triazine polymer (Polymer 3) and also a possible scheme for the synthesis of this polymer by polycondensation of a monomer A3 in accordance with the invention with a second monomer B3 not in accordance with the invention (FIG. 10);
- two other examples of triazine polymers (Polymer 4A and Polymer 4B) and also a possible scheme for the synthesis of these polymers by polycondensation of a monomer A4 in accordance with the invention with two other monomers B4 and C4 not in accordance with the invention (FIG. 11);
- another example of a triazine polymer (Polymer 5) and also a possible scheme for the synthesis of this polymer by polycondensation of a monomer A5 in accordance with the invention with a second monomer A5a in accordance with the invention (FIG. 12);
- another example of a triazine polymer (Polymer 7) and also a possible scheme for the synthesis of this polymer by polycondensation of a monomer A7 in accordance with the invention with a second monomer B7 not in accordance with the invention (FIG. 13);
- another example of a triazine polymer (Polymer 8) and also a possible scheme for the synthesis of this polymer by polycondensation of a monomer A8 in accordance with the invention with a second monomer B8 not in accordance with the invention (FIG. 14);
- a possible scheme for the synthesis, in three successive stages, of the monomer A1 (or Compound 3) in accordance with the invention of FIG. 8 (FIG. 15);
- the $^1$H NMR spectrum (360 MHz) of the Compound 3 (monomer A1) dissolved in $d_6$-DMSO (FIG. 16);
- a possible scheme for the synthesis, in three successive stages, of the monomer B1 (or Compound 6—M here representing $Na^+$) not in accordance with the invention of FIG. 8 (FIG. 17);
- the $^1$H NMR spectrum (500 MHz) of the Compound 6 (monomer B1) dissolved in $d_6$-DMSO (FIG. 18);
- a possible scheme for the synthesis, in three successive stages, of the monomer B8 (or Compound 9—M here representing $Na^+$) not in accordance with the invention of FIG. 14 (FIG. 19);
- the $^1$H NMR spectrum (500 MHz) of the Compound 9 (monomer B8) dissolved in $d_6$-DMSO (FIG. 20);
- the formula of Polymer 1 in the sulphonated and benzophenone-blocked form and also its $^1$H NMR spectrum (500 MHz), dissolved in $d_6$-DMSO (FIG. 21);
- the formula of Polymer 7 in the sulphonated and benzophenone-blocked form and also its $^1$H NMR spectrum (500 MHz), dissolved in $d_6$-DMSO (FIG. 22);
- electron microscopy photographs respectively recorded on a horizontal cross section (FIG. 23A) and a transverse cross section (FIG. 23B) of a PEM membrane consisting of Polymer 1 (FIG. 23);
- comparative polarization curves of a PEM fuel cell using the membrane resulting from Polymer 1 (curve $C_A$) and a commercial membrane (curve $C_B$) (FIG. 24).

IV. DETAILED DESCRIPTION OF THE INVENTION

The triazine monomer of the invention thus has the essential characteristic of corresponding to the formula (I):

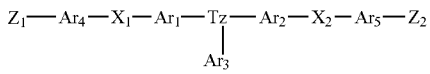

in which:
- the symbol Tz represents the 1,3,5-triazine nucleus;
- the symbols $X_1$ and $X_2$, which are identical or different, represent S, SO or $SO_2$;
- the symbols $Ar_1$, $Ar_2$, $Ar_4$ and $Ar_5$ which are identical or different, represent a substituted or unsubstituted phenylene group;
- the symbol $Ar_3$ represents a substituted or unsubstituted phenyl group;
- the symbols $Z_1$ and $Z_2$, which are identical or different, are selected from the group consisting of halogens, hydroxyl, alkoxyls, thiol, carboxyls, carboxylates, amino, sulphonamido, acyl chloride, sulphonyl chloride, sulphonyl fluoride, isocyanate and their mixtures.

It should be remembered here that 1,3,5-triazine (also known as "s triazine") has the formula:

The triphenyl-1,3,5-triazine is thus represented in the formula (I) by:

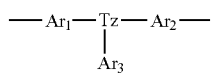

In other words, the triazine monomer of the invention of formula (I) thus has the expanded formula (the symbol R here representing hydrogen or a replacement for the hydrogen):

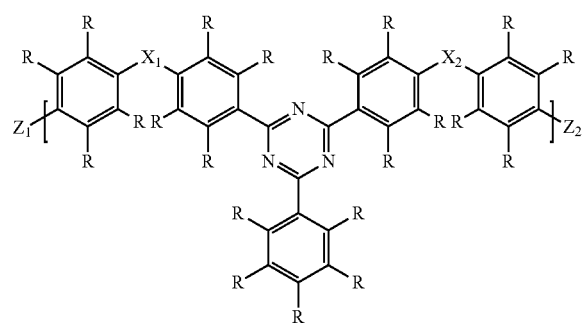

Figure 1B:
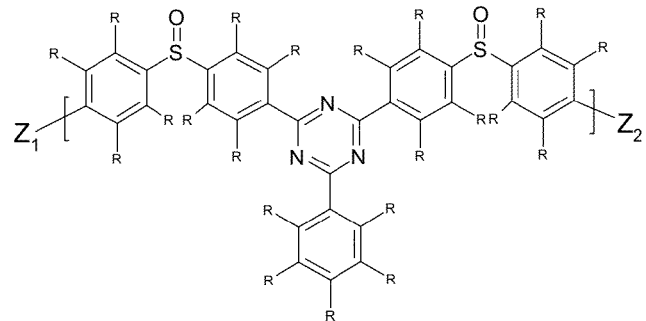
Figure 1C:
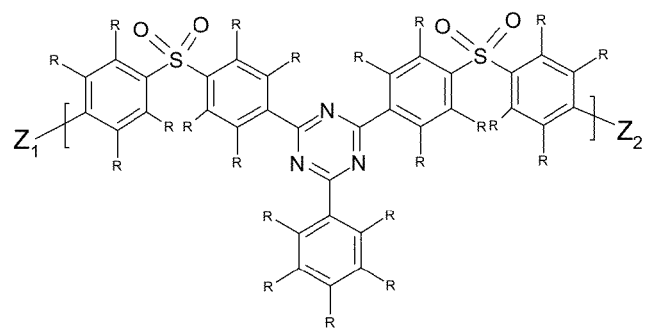
Figure 2A:
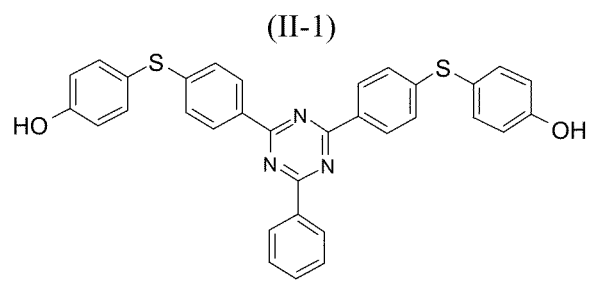
Figure 2B:
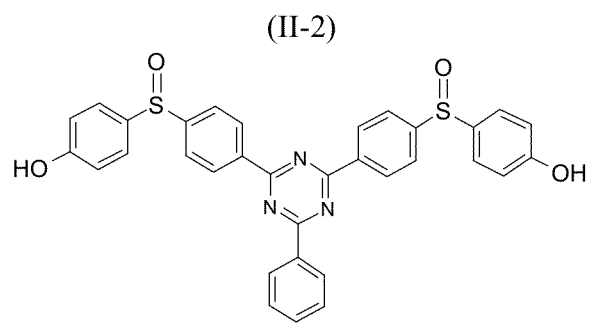
Figure 2C:
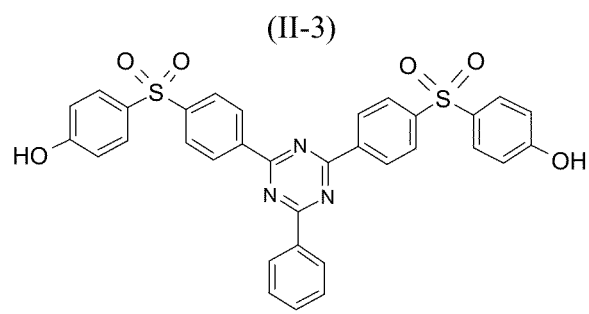

In other words, in the preferred case where $X_1$ and $X_2$ are identical, the triazine monomer of the invention of formula (I) corresponds to one of the three formulae I-1, I-2 and I-3 respectively represented in the appended FIGS. 1A, 1B and 1C.

As indicated above, the phenyl or phenylene groups $Ar_1$, $Ar_2$, $Ar_3$, $Ar_4$ and $Ar_5$ can be substituted or unsubstituted.

When they are substituted, the invention applies in particular to the cases where just one phenyl or phenylene group per triazine monomer of formula (I) is substituted as well as to the cases where several phenyl or phenylene groups per triazine monomer are substituted, it being possible for just one substituent or several identical or different substituents to be present on the same phenyl or phenylene group(s).

Mention may in particular be made, as examples of possible substituents of the aromatic nuclei (that is to say, more precisely possible replacements of the hydrogen atoms of these phenyl or phenylene groups), of the following substituents:

—F; —Cl; —Br; —CN; —$CF_3$; —$NO_2$; —$N(CH_3)_2$;
—COOH; —COOM; —$PO_3H$; —$PO_3M$; —$SO_3H$;
—$SO_3M$ (the symbol M representing an alkali metal cation, preferably $Na^+$ or $K^+$);
hydroxyl, alkyl, cycloalkyl, perfluoroalkyl, sulphoalkyl, sulphoaryl, aryl, alkylcarbonyl, arylcarbonyl, alkoxyl or aryloxyl radicals.

These possible substituents are preferably selected from the group consisting of the substituents —F, —CN, —$CF_3$, —$PO_3H$, —$PO_3M$, —$SO_3H$ and —$SO_3M$ and the mixtures of these substituents.

$Z_1$ and $Z_2$, which are identical or different, are selected from the group consisting of halogens (such as F, Cl, Br or I), hydroxyl (OH), alkoxyls (OR), thiol (SH), carboxyls (COOH), carboxylates (COOR), thiol (SH), amino ($NH_2$), sulphonamido ($SO_2$—$NH_2$), acyl chloride (CO—Cl), sulphonyl chloride ($SO_2$—Cl), sulphonyl fluoride ($SO_2$—F), isocyanate (NCO) and their mixtures.

More preferably, $Z_1$ and $Z_2$, which are identical or different, are selected from the group consisting of halogens (such as F, Cl, Br or I), hydroxyl (OH), thiol (SH) and their mixtures.

Thus, according to a specific and preferred embodiment, $Z_1$ and $Z_2$ correspond to the hydroxyl group. In the preferred case where $X_1$ and $X_2$ are identical, the triazine monomer of the invention of formula (I) is thus 2,4-[4-(4-hydroxyphenylsulphanyl)phenyl]-6-phenyl-1,3,5-triazine, 2,4-[4-(4-hydroxyphenylsulphoxy)phenyl]-6-phenyl-1,3,5-triazine or 2,4-[4-(4-hydroxyphenylsulphonyl)phenyl]-6-phenyl-1,3,5-triazine, respectively corresponding to the three formulae II-1, II-2 and II-3 represented in the appended FIGS. 2A, 2B and 2C, in which the phenylene or phenyl groups may or may not be substituted.

Figure 3A:
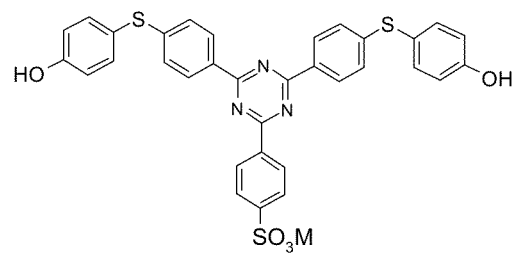
Figure 3B:
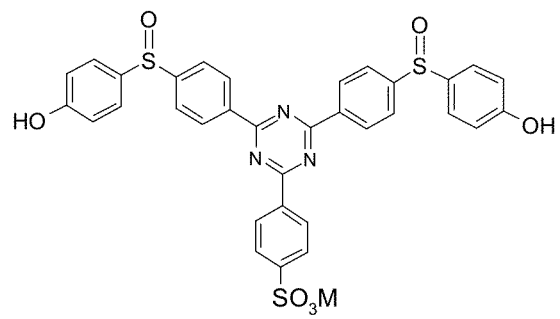
Figure 3C:
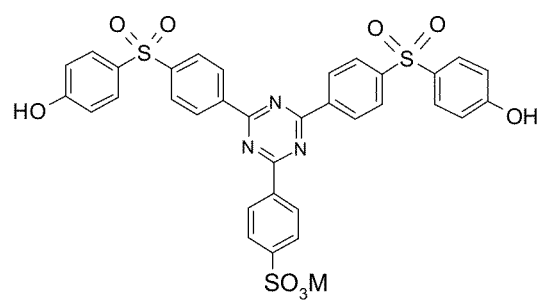

The appended FIGS. 3A, 3B and 3C represent more specific examples of triazine monomers in accordance with the invention, in the sulphonated form, of respective formulae II-1-A, II-2-A and II-3-A, in which $X_1$ and $X_2$ are identical, $Z_1$ and $Z_2$ correspond to the hydroxyl group and just one of the phenylene or phenyl groups (in this instance, as example, the pendant phenyl group $Ar_3$) is substituted by a sulphonate group $SO_3M$ (M representing an alkali metal cation, preferably $Na^+$ or $K^+$); they are thus more specifically, and respectively, alkali metal salts of 2,4-[4-(4-hydroxyphenylsulphanyl)phenyl]-6-(p-sulphonatophenyl)-1,3,5-triazine, of 2,4-[4-(4-hydroxyphenylsulphoxy)phenyl]-6-(p-sulphonatophenyl)-1,3,5-triazine and of 2,4-[4-(4-hydroxyphenylsulphonyl)phenyl]-6-(p-sulphonatophenyl)-1,3,5-triazine.

Figure 4A:
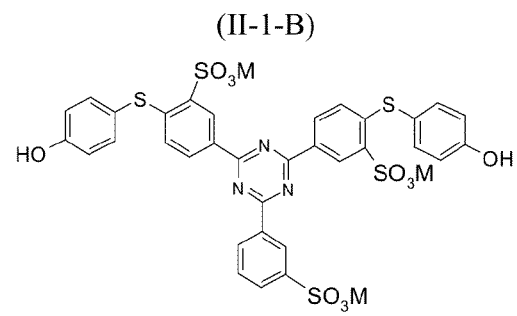
Figure 4B:
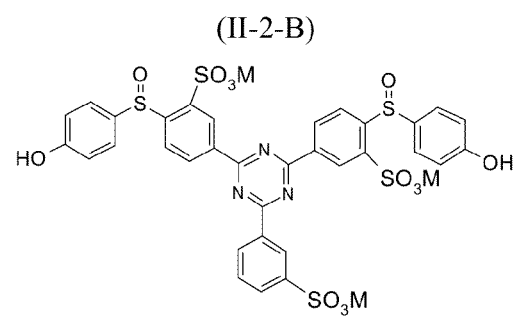
Figure 4C:
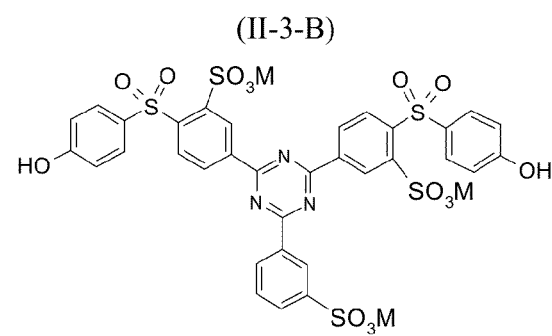

The appended FIGS. 4A, 4B and 4C represent other more specific examples of triazine monomers in accordance with the invention, in the sulphonated form, of respective formulae II-1-B, II-2-B and II-3-B, in which $X_1$ and $X_2$ are identical, $Z_1$ and $Z_2$ correspond to the hydroxyl group and three of the phenylene or phenyl groups (in this instance, as example, the $Ar_1$, $Ar_2$ and $Ar_3$ groups) are substituted by a sulphonate group SO₃M (M representing an alkali metal cation, preferably Na⁺ or K⁺); they are thus in this instance more specifically, and respectively, alkali metal salts of 2,4-bis[4-(4-hydroxyphenylsulphanyl)-3-sulphonatophenyl]-6-(m-sulphonatophenyl)-1,3,5-triazine, of 2,4-bis[4-(4-hydroxyphenylsulphoxy)-3-sulphonatophenyl]-6-(m-sulphonatophenyl)-1,3,5-triazine and of 2,4-bis[4-(4-hydroxyphenylsulphonyl)-3-sulphonatophenyl]-6-(m-sulphonatophenyl)-1,3,5-triazine.

According to another specific and preferred embodiment, $Z_1$ and $Z_2$, which are identical or different, correspond to a halogen selected in particular from the group consisting of fluorine, chlorine, bromine and the mixtures of such halogens, more particularly still from fluorine, chlorine and the mixtures of such halogens.

Thus, according to a particularly preferred implementational example, $Z_1$ and $Z_2$ correspond to the halogen fluorine, that is to say that the triazine monomer of the invention then corresponds to the formula:

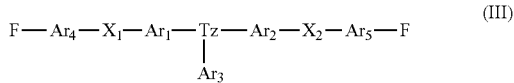
(III)

Figure 5A:
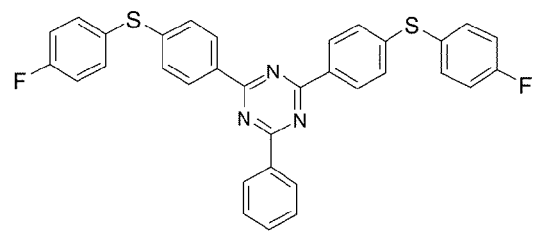
Figure 5B:
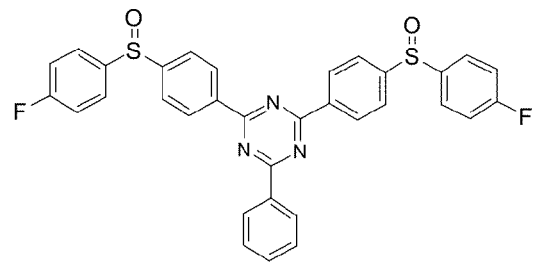
Figure 5C:
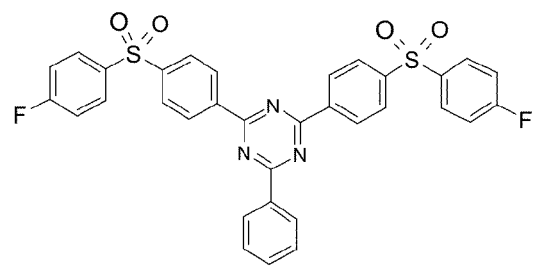

Thus, in the more preferred case where $X_1$ and $X_2$ are identical, the triazine monomer of the invention of formula (I) is thus 2,4-[4-(4-fluorophenylsulphanyl)phenyl]-6-phenyl-1,3,5-triazine, 2,4-[4-(4-fluorophenylsulphoxy)phenyl]-6-phenyl-1,3,5-triazine or 2,4-[4-(4-fluoro-phenylsulphonyl)phenyl]-6-phenyl-1,3,5-triazine, respectively corresponding to the formulae III-1, III-2 and III-3 represented in the appended FIGS. 5A, 5B and 5C, in which the phenylene or phenyl groups may or may not be substituted.

Figure 6A:
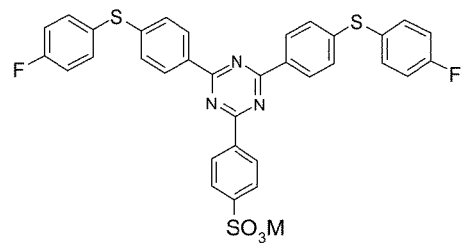
Figure 6B:
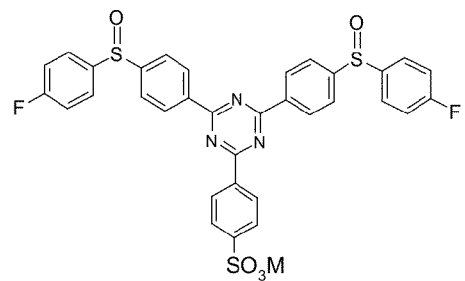
Figure 6C:
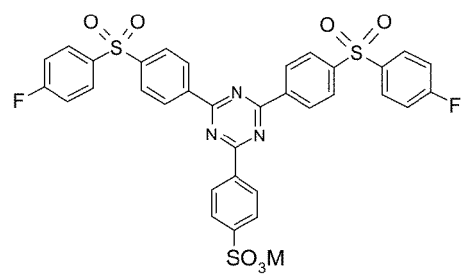

The appended FIGS. 6A, 6B and 6C represent more specific examples of triazine monomers in accordance with the invention, in the sulphonated form, of respective formulae III-1-A, III-2-A and III-3-A, in which $X_1$ and $X_2$ are identical, $Z_1$ and $Z_2$ correspond to fluorine and just one of the phenyl groups (in this instance, as example, the pendant phenyl group $Ar_3$) is substituted by a sulphonate group SO₃M (M representing an alkali metal cation, preferably Na⁺ or K⁺); they are thus in this instance more specifically, and respectively, alkali metal salts of 2,4-[4-(4-fluorophenylsulphanyl)phenyl]-6-(p-sulphonatophenyl)-1,3,5-triazine, of 2,4-[4-(4-fluorophenylsulphoxy)phenyl]-6-(p-sulphonatophenyl)-1,3,5-triazine, and of 2,4-[4-(4-fluorophenylsulphonyl)phenyl]-6-(p-sulphonatophenyl)-1,3,5-triazine.

The appended FIGS. 7A, 7B and 7C represent other more specific examples of triazine monomers in accordance with the invention, in the sulphonated form, of respective formulae III-1-B, III-2-B and III-3-B, in which $X_1$ and $X_2$ are identical, $Z_1$ and $Z_2$ correspond to fluorine and three of the phenyl groups (in this instance, as example, the phenyl groups $Ar_1$, $Ar_2$ and $Ar_3$) are substituted by a sulphonate group SO₃M (M representing an alkali metal cation, preferably Na⁺ or K⁺); they are thus here more specifically, and respectively, alkali metal salts of 2,4-bis[4-(4-fluorophenylsulphanyl)-3-sulphonatophenyl]-6-(m-sulphonatophenyl)-1,3,5-triazine, of 2,4-bis[4-(4-fluorophenylsulphoxy)-3-sulphonatophenyl]-6-(m-sulphonatophenyl)-1,3,5-triazine and of 2,4-bis[4-(4-fluorophenylsulphonyl)-3-sulphonatophenyl]-6-(m-sulphonatophenyl)-1,3,5-triazine.

According to another particularly preferred implementational example, the $Z_1$ and $Z_2$ groups correspond to chlorine, that is to say that the triazine monomer of the invention then corresponds to the formula:

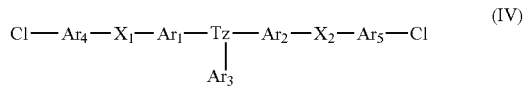
(IV)

Thus, in the more preferred case where $X_1$ and $X_2$ are identical, the triazine monomer of the invention of formula (I) corresponds to one of the three formulae III-1, III-2 and III-3 represented above in the appended FIGS. 5A, 5B and 5C respectively but in which chlorine replaces fluorine. In particular, the triazine monomer of the invention corresponds to one of the formulae III-1-A, III-2-A, III-3-A, III-1-B, III-2-B and III-3-B, represented above in the appended FIGS. 6A, 6B, 6C, 7A, 7B and 7C respectively but in which chlorine replaces fluorine.

The triazine monomer in accordance with the invention described above can advantageously be used for the synthesis of triazine polymers which can form, in the sulphonated form, an electrolyte (or membrane, which is equivalent) in a fuel cell. The term "polymer" should be understood as meaning any homopolymer or copolymer, in particular block copolymer, comprising structural components resulting from the monomer of the invention.

The term "sulphonated monomer" or "sulphonated polymer" is understood to mean, by definition and in a well known way, a monomer or polymer bearing one or more sulphonic (—SO₃H) or sulphonate (—SO₃M) groups or mixtures of such groups, M representing a cation of an alkali metal preferably chosen from lithium (Li), cesium (Cs), sodium (Na) and potassium (K), more preferably from sodium (Na) and potassium (K). It will be restated briefly here that it is the sulphonic groups which, in a PEM cell, provide the proton conductivity of the polymer used as membrane. Preferably, the sulphonic or sulphonate group is borne by at least one phenyl or phenylene group or, if appropriate, by at least one substituent of the phenyl or phenylene groups.

The appended FIGS. 8 to 14 represent several examples of polymers which can be synthesized from triazine monomers of formula (I) in accordance with the invention, and also various possible schemes for the synthesis of these polymers from these monomers.

The triazine polymer (hereinafter referred to as "Polymer 1") as represented in FIG. 8 (in the sulphonated form) is composed of two types of triazine-based structural units connected to one another via ether (—O—) bridges. This Polymer 1 can be prepared by polycondensation of a monomer in accordance with the invention, denoted A1 in FIG. 8, with a second monomer, denoted B1 (disulphonated, not in accordance with the invention), in the presence of a base and of an organic solvent, according to a procedure which will be described in detail later. It should be noted that the monomer A1 corresponds to the triazine monomer of formula (II-3) described above (FIG. 2C).

Figure 9:
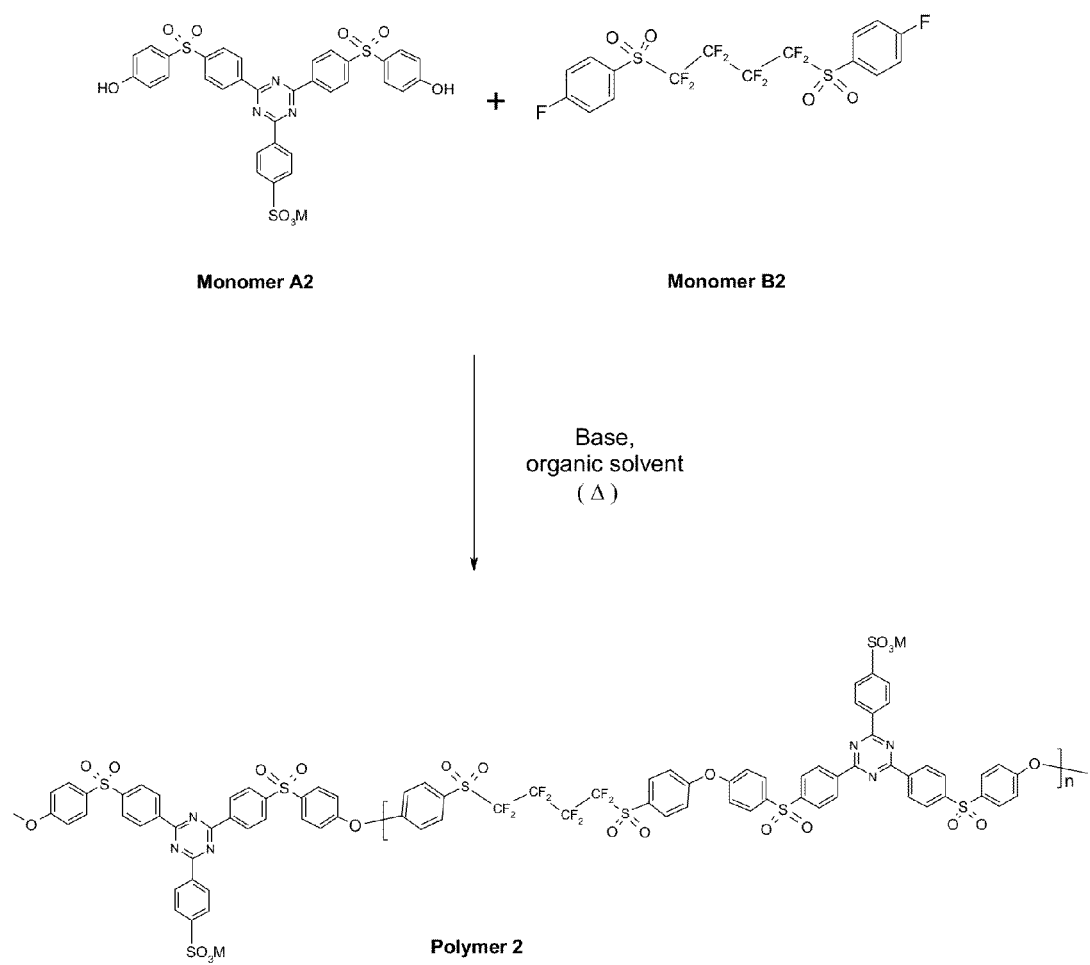

The triazine polymer (hereinafter referred to as "Polymer 2") as represented in FIG. 9 (also in the sulphonated form) is itself also composed of two types of triazine-based structural units connected to one another via ether (—O—) bridges. This Polymer 2 can be prepared by polycondensation of a monomer (sulphonated) in accordance with the invention, denoted A2 in FIG. 9, with a second monomer (not in accordance with the invention), denoted B2, in the presence of a base and of an organic solvent. It should be noted that the monomer A2 corresponds to the triazine monomer of formula (II-3-A) described above (FIG. 3C).

Figure 10:
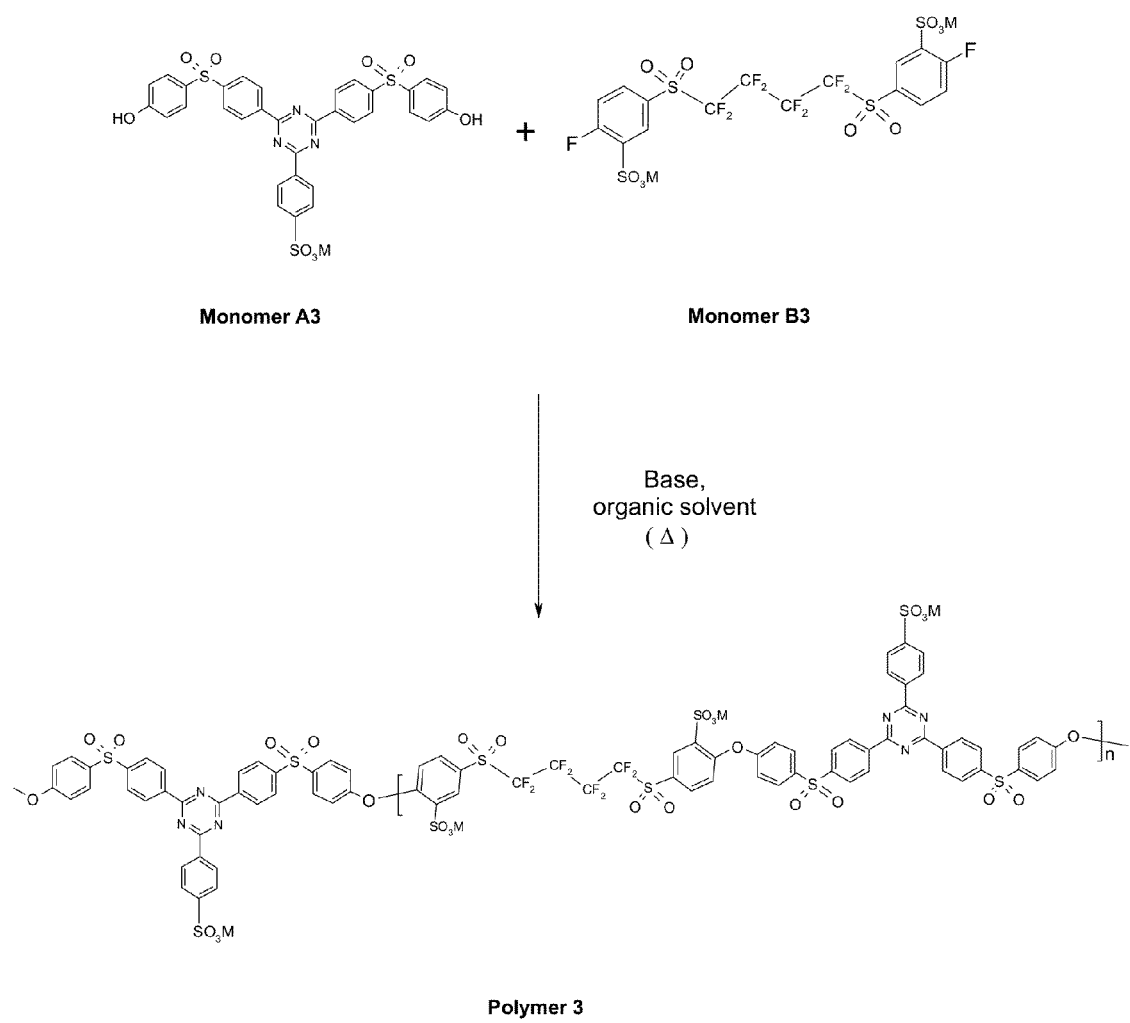

The triazine polymer (hereinafter referred to as "Polymer 3") as represented in FIG. 10 (also in the sulphonated form) is itself also composed of two types of triazine-based structural units connected to one another via ether (—O—) bridges. This Polymer 3 can be prepared by polycondensation of a monomer (sulphonated) in accordance with the invention, denoted A3 in FIG. 10, with a second monomer (disulphonated, not in accordance with the invention), denoted B3, in the presence of a base and of an organic solvent. It should be noted that the monomer denoted A3 (in order to standardize the references in the different figures) also corresponds to the monomer denoted A2 of the preceding figure.

Figure 11:
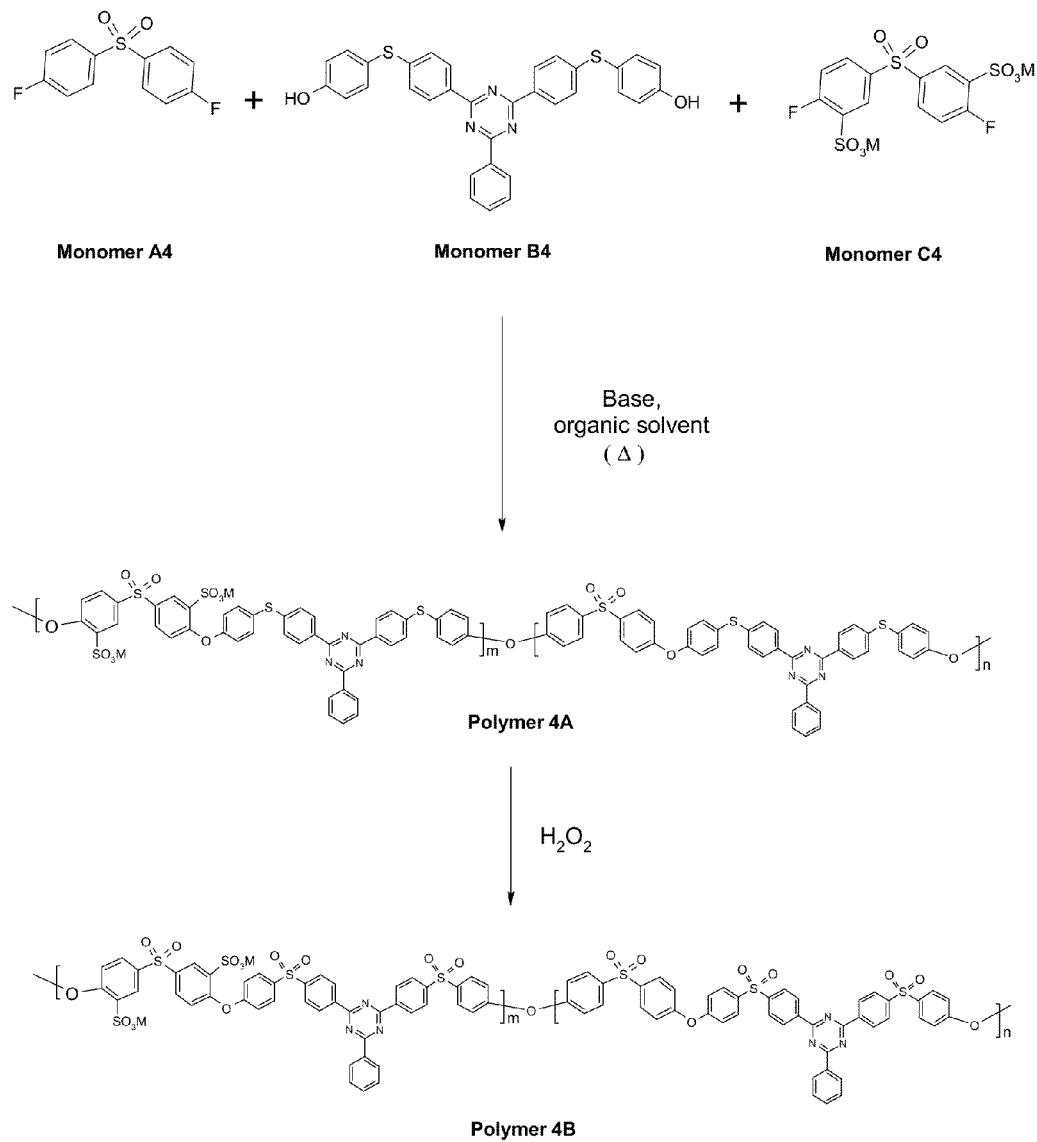

The triazine polymers (hereinafter referred to as "Polymer 4A" and "Polymer 4B") of FIG. 11 (also in the sulphonated form) are themselves also composed of two types of triazine-based structural units connected to one another via ether (—O—) bridges. These Polymers 4A and 4B can be prepared by copolymerization of a monomer in accordance with the invention, denoted A4, with two other monomers not in accordance with the invention, denoted B4 and C4 (disulphonated monomer C4) in FIG. 11, in the presence of an appropriate base and of an appropriate organic solvent, as above for Polymers 1, 2 or 3. The first polymer (Polymer 4A) thus obtained is subsequently oxidized with hydrogen peroxide (aqueous hydrogen peroxide solution) in order to obtain the final polymer (Polymer 4B). The monomers B4 and C4 are known, commercially available. The monomer A4 in accordance with the invention is prepared according to a procedure which will be described in detail subsequently; this monomer A4 corresponds to the triazine monomer of formula (II-1) described above (FIG. 2A).

Figure 12:
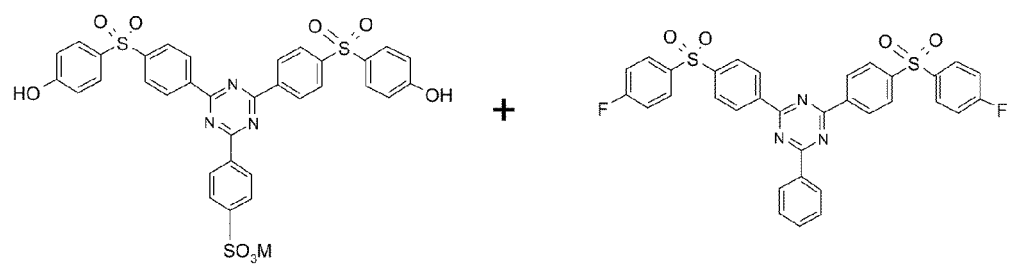
Figure 12:
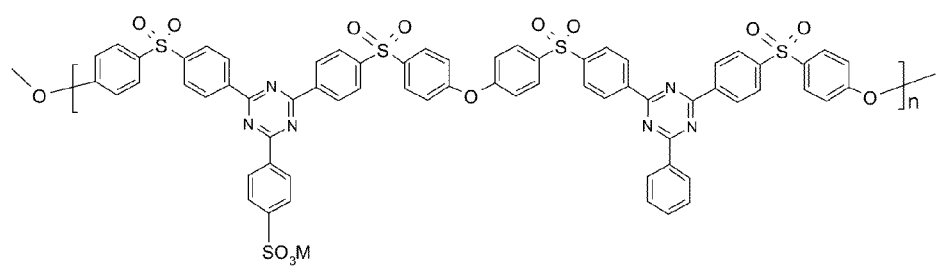

The triazine polymer (hereinafter referred to as "Polymer 5") of FIG. 12 (also in the sulphonated form) is for its part composed of the same triazine-based structural units connected to one another via ether (—O—) bridges. This Polymer 5 can be prepared by polycondensation of a monomer (sulphonated) according to the invention, denoted A5 in FIG. 12, with a second monomer also in accordance with the invention, denoted A5a. The monomer denoted A5 (in order to standardize the references in the figures) is in fact identical to the triazine monomers denoted A2 and A3 in the preceding figures; the monomer A5a corresponds to the triazine monomer of formula (III-3) described above (FIG. 5C).

The triazine polymer (hereinafter referred to as "Polymer 7") of FIG. 13 (also in the sulphonated form) is itself also composed of two types of triazine-based structural units connected to one another via ether (—O—) bridges. This Polymer 7 can be prepared by polycondensation of a monomer in accordance with the invention, denoted A7 in FIG. 13, with a second monomer (disulphonated) not in accordance with the invention, denoted B7, in the presence of a base and of an organic solvent, according to a procedure which will be described in detail later. The monomer denoted A7 (in order to standardize the references in the figures) is identical to the triazine monomer denoted A4 in the preceding FIG. 11, the monomer B7 for its part being identical to the monomers B1 and B3 of FIGS. 8 and 10.

The triazine polymer (hereinafter referred to as "Polymer 8") of FIG. 14 (also in the sulphonated form) is itself also composed of two types of triazine-based structural units connected to one another via ether (—O—) bridges. This Polymer 8 can be prepared by polycondensation of a monomer in accordance with the invention, denoted A8 in FIG. 14, with a second monomer (disulphonated) not in accordance with the invention, denoted B8, in the presence of a base and of an organic solvent, according to a procedure which will be described in detail later. The monomer denoted A8 (in order to standardize the references in the figures) is identical to the triazine monomers denoted A4 and A7 in the preceding FIGS. 11 and 13. In this instance, the triazine polymer comprises chain ends blocked by hydrophobic and stearically hindering benzophenone blocking groups (denoted B in FIG. 14) intended to reduce the solubility of the polymer in water.

V. EXAMPLES OF THE IMPLEMENTATION OF THE INVENTION

The tests which follow first of all describe in detail the synthesis of the monomers A1, B1 (also referred to as B7), A7 (also referred to as A4 and A8) and B8, and then that of the Polymer 1, Polymer 7 and Polymer 8.

Subsequently, the Polymer 1 is characterized and tested as a proton-conducting membrane in a fuel cell of the PEM type.

In the present description, unless expressly indicated otherwise, all the percentages (%) shown are % by weight.

V-1. Synthesis of the Monomer A1

The monomer A1 is 2,4-[4-(4-hydroxyphenylsulphonyl)phenyl]-6-phenyl-1,3,5-triazine, the formula II-3 of which (already reproduced in FIG. 2C and FIG. 8) is as follows:

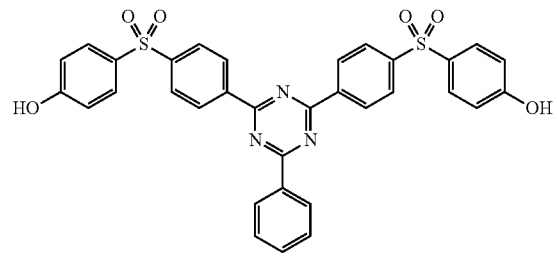 [SMILES: O=S(=O)(c1ccc(O)cc1)c1ccc(-c2nc(-c3ccccc3)nc(-c3ccc(S(=O)(=O)c4ccc(O)cc4)cc3)n2)cc1]

This monomer A1 (or Compound 3 in FIG. 15) was prepared according to the procedure represented diagrammatically in FIG. 15, in three successive stages, as described in detail below.

V-1-A) Stage 1

Figure 15A:
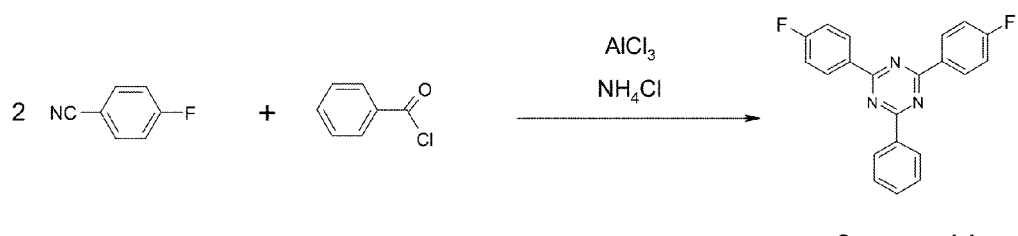

During a first stage, the Compound 1 or 2,4-bis(p-fluorophenyl)-6-phenyl-1,3,5-triazine is prepared according to the procedure which follows and which is represented diagrammatically in FIG. 15A.

This procedure, although different, is inspired by the process for the synthesis of chlorinated triphenyltriazines as described in the publication by Spencer R. D. & Beggs B. H, "*Determination of Four Closely Related Triaryl-s-Triazines by Infrared Spectroscopy*", Anal. Chem., 1963, 31(11), 1633-1636.

A 500 ml three-necked round-bottomed flask, equipped with a magnetic bar, a reflux condenser and a thermometer, is dried using a hot-air gun (the apparatus is placed under vacuum). 67.8 g of p-fluorobenzonitrile (0.56 mol) (Fluorochem 99%), 36.0 g of ammonium chloride (0.68 mol), 34.0 g of aluminium chloride (0.26 mol) and 32.0 g of benzoyl chloride (0.22 mol) are placed in the round-bottomed flask under nitrogen. The round-bottomed flask is immersed in an oil bath heated to 158° C. and is left overnight at 150° C. (temperature inside the reaction round-bottomed flask), a gentle stream of nitrogen above the reaction mixture.

The reaction product is cooled to ambient temperature (approximately 23° C.) and hydrolysed by adding 300 g of ice and 60 g of 36% HCl. The solid is filtered off, then dispersed in water and washed until a neutral pH is obtained. The white solid is stirred in 500 ml of methanol heated at reflux for 30 min and then the mixture is allowed to cool to ambient temperature. To finish, the product is filtered off and dried at 60° C. under vacuum. 26.6 g (yield 35%) of Compound 1 are thus obtained, which compound exhibits a melting point (according to DSC) of 254.5° C.

The NMR analysis gives the following results:
$^1$H NMR, 500 MHz (CD$_2$Cl$_2$): 7.30-7.34 (m, 4H), 7.62-7.65 (m, 2H), 7.68-7.70 (m, 1H), 8.79-8.80 (d, 2H), 8.82-8.85 (m, 4H).

V-1-B) Stage 2

Figure 15B:
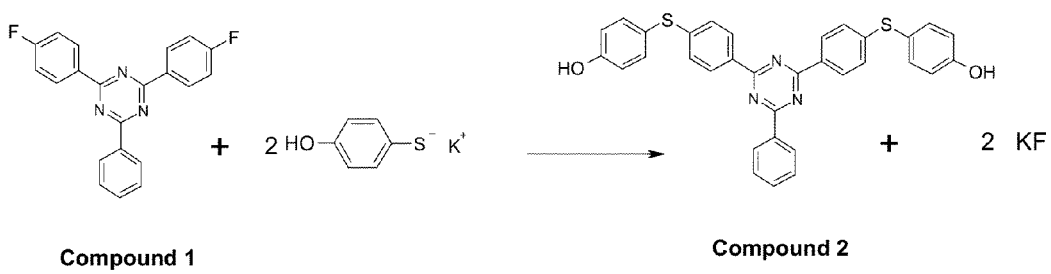

During a second stage, the Compound 2 in accordance with the invention (also referred to as monomer A4—see, for example, FIG. 11) or 2,4-[4-(4-hydroxyphenylsulphanyl)phenyl]-6-phenyl-1,3,5-triazine is prepared according to the procedure which follows and which is represented diagrammatically in FIG. 15B.

4-Hydroxythiophenol (or 4-HTP) (99%, Acros) is stored under nitrogen and in solid form. The Compound 1 and K$_2$CO$_3$ are dried separately overnight at 150° C. under vacuum. A magnetic bar is placed in a 2 l round-bottomed flask (equipped with a reflux condenser, a thermometer and a nitrogen inlet/outlet). The apparatus is placed under vacuum and dried. A two-way valve is used to replace the vacuum with nitrogen and to continually purge with the inert gas during the addition of the reactants.

The Compound 1 (9.13 g, i.e., 26.44 mmol) and powdered anhydrous K$_2$CO$_3$ (9.69 g, i.e., 1.2 eq. with respect to the 4-HTP) are added, while still hot (at the end of drying), to the apparatus purged with nitrogen. This is followed by the addition of 750 ml of anhydrous DMSO. The suspension obtained is subsequently purged for at least 15 min with a stream of nitrogen inside the solution.

The required amount of 4-HTP (7.45 g or 58.42 mmol, i.e., 2.2 eq.), in the liquid form, is transferred using a 10 ml plastic syringe, weighed directly inside the syringe and injected into the reaction mixture. Once all the reactants are added, the nitrogen is purged continuously above the solution. The mixture is heated at 100° C. overnight (20 hours) with continuous stirring and is then allowed to cool to ambient temperature.

The product cannot be purified in a single stage: approximately 250 ml of aliquot fraction of the reaction mixture are withdrawn and poured into a separation funnel (3 liters) containing 2.6 liters of ethyl acetate/water (ratio by weight 1/1). The remainder of the product is kept under a continual stream of nitrogen. The mixture placed in the separation funnel is shaken (the colour changes from orange to lemon yellow) and the desired product is extracted into the ethylene acetate phase (the DMSO/H$_2$O phase comprises only traces of the desired product). The organic phase is washed with 100 ml of an NaHCO$_3$ solution, which stage is followed by washing with 100 ml of H$_2$O; the organic phase is subsequently dried with anhydrous MgSO$_4$. The process is repeated twice with the other two remaining 250 ml aliquots of the reaction mixture.

The ethyl acetate phase is evaporated using a rotary evaporator; a viscous slightly orange liquid, like honey, remains (comprising a small amount of DMSO). The residual DMSO is removed at 100° C. under reduced pressure. A small amount of acetone (10 ml) is added, followed by 40 ml of diethyl ether. The solid immediately becomes cream white and is filtered off on a ceramic filter. The residual thiol is removed from the reaction product by column chromatography using hexane/CH$_2$Cl$_2$/ethyl acetate/methanol (ratios by weight 4/2/1/1) as mobile phase.

13.1 g (i.e., a yield of approximately 89%) of the Compound 2 are thus obtained.

The NMR analysis gives the following results:
$^1$H NMR (500 MHz) d$_6$-DMSO: 6.93-6.95 (d, 4H), 7.17-7.19 (d, 4H), 7.42-7.44 (d, 4H), 7.58-7.60 (m, 2H), 7.65-7.68 (m, 1H), 8.49-8.50 (d, 4H), 8.61-8.63 (d, 2H), 10.04 (s, 2H).

The molecular weight of the product, as measured by "MALDI" (Matrix-assisted Laser Desorption/Ionization) mass spectrometry (positive mode; dithranol matrix), is equal to 558.1 (calculated theoretical value equal to 557.7).

V-1-C) Stage 3

Figure 15C:
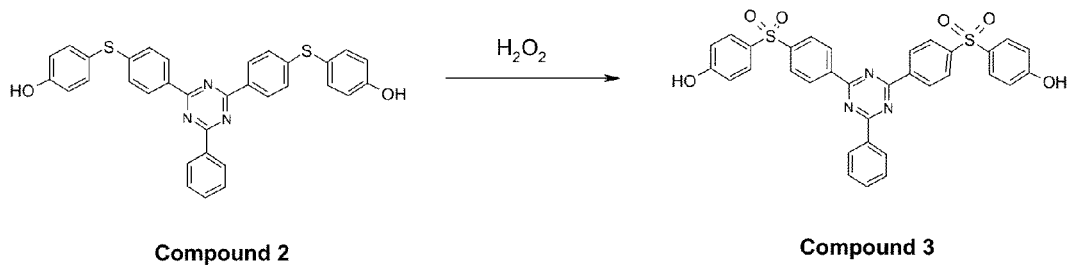

Finally, during a third and final stage, the Compound 3 in accordance with the invention (monomer A1) is prepared according to the procedure which follows and which is represented diagrammatically in FIG. 15C.

A 250 ml three-necked round-bottomed flask is equipped with a magnetic bar, a thermometer, a reflux condenser and an opening used for the addition of the reactants. A suspension is prepared by adding 6.69 g of Compound 2 (12 mmol) to 150 ml of glacial acetic acid. Once the reactant has been added, the suspension is heated to 70° C. The reactant dissolves, giving a slight transparent yellow coloration. Subsequently, 18.0 g of 50% hydrogen peroxide (264 mmol) are introduced dropwise into the reaction (no exothermicity is observed). The solution is heated at reflux (100° C.) for 1 hour (slightly yellow coloration). Thin layer chromatography (silica plate) in CH$_2$Cl$_2$/ethyl acetate/methanol (ratios by weight 3/1/1) makes it possible to monitor the consumption of the reactant during the reaction (the blue fluorescence of the triazine at 325 nm disappears with the oxidation).

Subsequently, 50 ml of acetic acid are removed by distillation at reduced pressure (vacuum generated by a water pump). After distillation, during the cooling, white crystals begin to precipitate from the solution as soon as the temperature falls below 80° C. The solution is left overnight at ambient temperature in order for the product to crystallize from the acetic acid. The acetic acid is then removed by filtration and the final white product is washed with 300 ml of distilled water. Subsequently, approximately 18 g of wet product thus obtained are transferred into a round-bottomed flask and 75 ml of distilled water are added, the combined mixture being stirred for approximately 15 min. The product is subsequently filtered off and washed up to a value of neutral pH. The product, which is still wet, is dried at 60° C. under vacuum for 2 h and then at 100° C. under vacuum overnight (approximately 12 h).

Purification is carried out by column chromatography using CH$_2$Cl$_2$/ethyl acetate/methanol (3/1/1) as mobile phase.

The endothermic peak lies at approximately 294° C. (1$^{st}$ DSC run). It is recorded that the monomer immediately polymerizes during the second DSC run; the glass transition temperature (Tg) of the polymer thus formed lies at approximately 145° C.

5.35 g (yield of approximately 80%) of the Compound 3 or monomer A1 are thus obtained.

Figure 16:
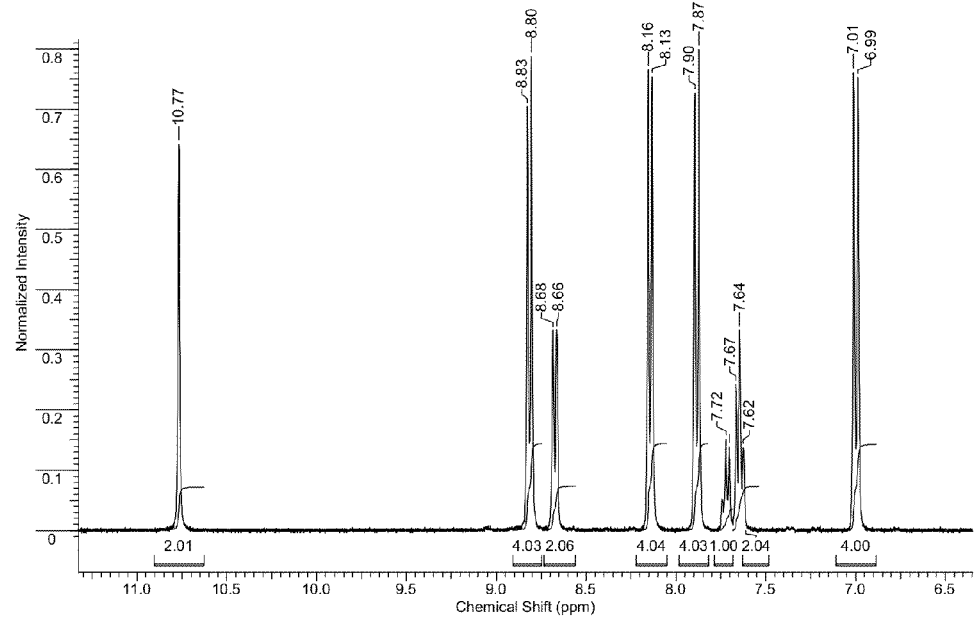

The $^1$H NMR spectrum (360 MHz) of the monomer A1 in accordance with the invention thus obtained, dissolved in d$_6$-DMSO, is reproduced in FIG. 16.

The NMR analysis gives the following results:
$^1$H NMR (360 MHz) d$_6$-DMSO: 6.99-7.01 (d, 4H), 7.62-7.67 (m, 2H), 7.72 (t, 1H), 7.87-7.90 (d, 4H), 8.13-8.16 (d, 4H), 8.66-8.68 (d, 2H), 8.80-8.83 (d, 4H), 10.77 (s, 2H).

Finally, the molecular weight of the product, as measured by "ESI" (Electrospray Ionization) mass spectrometry (negative mode; water/acetone 1/1 mixture), is equal to 620.7 (calculated theoretical value equal to 621.7).

V-2. Synthesis of the Monomer B1

The monomer B1, to recapitulate, not in accordance with the present invention, is disulphonated 3,3'-bis(4-fluorophenylsulphonyl)perfluorobutane, the formula of which (already reproduced in FIG. 8) is as follows:

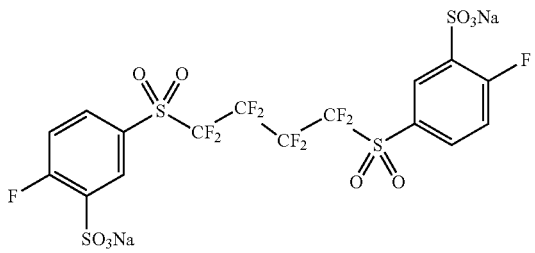

This monomer B1 (or Compound 6 in FIG. 17) was prepared according to the procedure represented diagrammatically in FIG. 17, in three successive stages, as described in detail below.

V-2-A) Stage 1

Figure 17A:
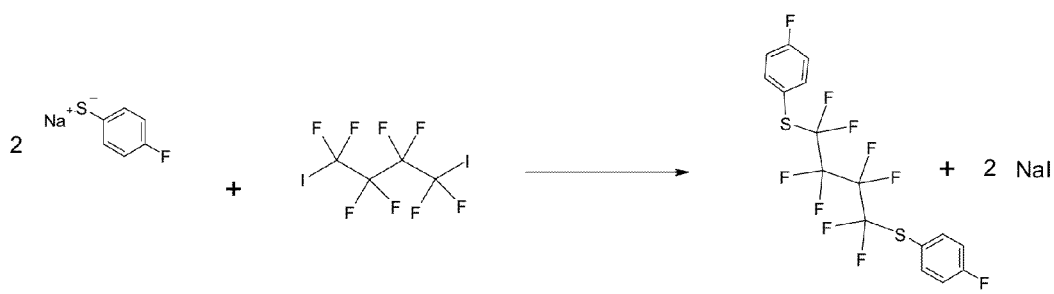

During a first stage, the Compound 4 or 1,4-bis(4-fluorophenylthio)perfluorobutane is prepared according to the procedure which follows and which is represented diagrammatically in FIG. 17A.

This procedure, although different, is inspired by the process for the synthesis of fluorinated polyethersulphones, as described in the publication by Feiring A. E., Wonchoba E. R. & Arthur R. D., "*Fluorinated Poly(Ether Sulfone)s*", J. Polym. Sci., Part A: Pol. Chem., 1990, 38, 2809-2818.

A mixture of sodium methoxide (13.64 g) (Fluka, 97%) and 4-fluorothiophenol (31.70 g) (Fluorochem, 99%) in 200 ml of anhydrous methanol is heated at reflux for 60 min. After distilling off the methanol, the white solid is kept under nitrogen in the apparatus at ambient temperature.

51.0 g of 1,4-diiodoperfluorobutane (0.110 mol) (Apollo Scientific, 98%) are added to a solution of 37.0 g of sodium 4-fluorophenylthiolate salt (244.83 mmol) in 170 ml of anhydrous DMF, under nitrogen and cooled to 0° C.; an exothermicity occurs and the temperature reaches 40° C. The solution obtained is kept at 40° C. and stirred (approximately 12 hours). It is subsequently heated at 60° C. for 1 hour. The solution, once it has returned to ambient temperature, is diluted with 60 ml of water and then concentrated using a vacuum pump in order to remove 100 ml of solvent. The remaining solution is diluted with water and the lower phase is separated and washed with water. The product is distilled at 120° C. under vacuum. After having removed the impurities, a colourless liquid is recovered, i.e., 37.9 g (75.6%). The remaining traces of impurities (thiol) are removed by column chromatography using hexane as mobile phase, giving a product resembling solid and transparent wax at ambient temperature. The melting point of the product is equal to approximately 50° C. (measured by DSC).

The Compound 4, of formula:

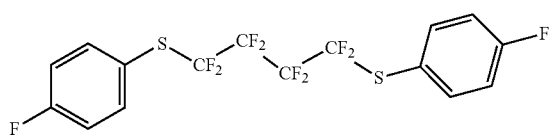 [SMILES: Fc1ccc(SC(F)(F)C(F)(F)C(F)(F)C(F)(F)Sc2ccc(F)cc2)cc1]

is thus obtained.

The NMR analysis gives the following results:
$^1$H NMR, 500 MHz (CDCl$_3$): 7.09-7.12 (m, 4H), 7.62-7.65 (m, 4H).

V-2-B) Stage 2

Figure 17B:
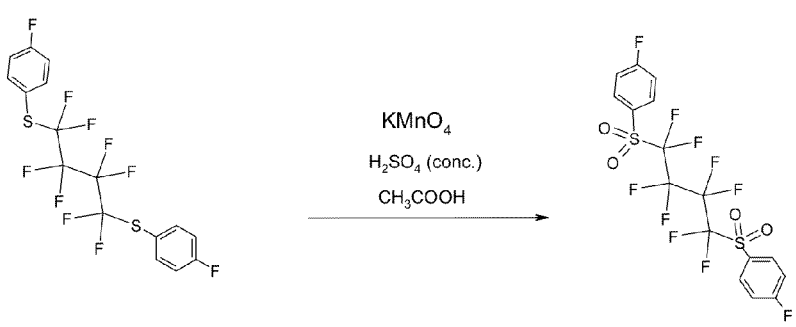

Then, during a second stage, the Compound 5 or 1,4-bis(4-fluoro-phenylsulphonyl)perfluorobutane is prepared according to the procedure which follows and which is represented diagrammatically in FIG. 17B.

A one liter two-necked round-bottomed flask, equipped with a reflux condenser, a magnetic bar and a nitrogen inlet, is charged with 31.80 g (80.0 mmol) of Compound 4, 350 ml of glacial acetic acid and 65.4 g (i.e., 413 mmol) of KMnO$_4$ (5.9 eq.). After stirring at ambient temperature for 10 min, the solution is cooled to between 0° C. and 5° C. and then 35 ml of concentrated sulphuric acid are added dropwise during the cooling with the ice bath (temperature of between 0 and 5° C., for 5 hours). The reaction mixture is stirred overnight at ambient temperature and is then poured into 3.5 liters of distilled water. The product is extracted with 7 liters of chloroform. The hydrolysed MnO$_2$ is filtered each time through a filter paper plus a textile filter. The solvent (chloroform/acetic acid) is removed using a rotary evaporator at 50° C. The product is then dissolved in 1 liter of chloroform. The organic phase is subsequently successively washed with 200 ml of a saturated NaHCO$_3$ solution and then with 200 ml of distilled water, and is finally dried with MgSO$_4$. The solvent is removed on a rotary evaporator and then the product is purified by column chromatography using a hexane/ethyl acetate/methanol (15/3/2) mixture as eluent, in order to obtain the Compound 5.

The product, in the form of white crystals, is dried overnight at 60° C. under vacuum. It is subsequently recrystallized from acetone in order to obtain transparent crystals. The DSC analysis reveals a melting point of approximately 127° C.

32.6 g (yield 90%) of Compound 5, of formula:

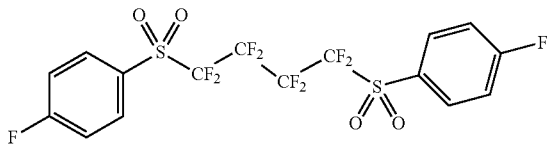 [SMILES: O=S(=O)(c1ccc(F)cc1)C(F)(F)C(F)(F)C(F)(F)C(F)(F)S(=O)(=O)c1ccc(F)cc1]

are thus obtained.

The NMR analysis gives the following results:
$^1$H NMR, 500 MHz (CDCl$_3$): 7.36-7.39 (m, 4H), 8.07-8.10 (m, 4H).

V-2-C) Stage 3

Figure 17C:
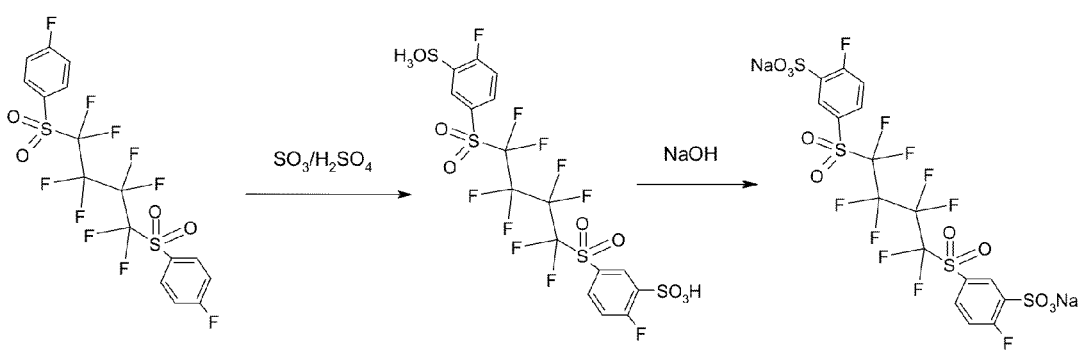

Finally, during a third and final stage, the Compound 6 or monomer B1 (disulphonated 3,3'-bis(4-fluorophenylsulphonyl)perfluorobutane) is prepared according to the procedure which follows and which is represented diagrammatically in FIG. 17C.

The Compound 5 (5.0 g, i.e. 9.65 mmol) is placed in a four-necked round-bottomed flask dried with a hot-air gun and then placed under nitrogen (glass-covered magnetic bar). The concentrated sulphuric acid (23.6 g) is subsequently added using a predried graduated glass cylinder. Most of the compound does not dissolve in the sulphuric acid at ambient temperature (the solution becomes slightly purple). Finally, 20.06 g of oleum (Merck product comprising 65% SO$_3$) are added using a predried graduated dropping funnel. The gas outlet bubbler is filled with concentrated sulphuric acid and the gaseous products are purged through an empty trap and then through a trap filled with 10% NaOH. The reaction medium is heated at 120° C. (temperature of the oil bath of 128° C.) with a moderate stream of nitrogen moving above the solution. The reaction is continued at 120° C. overnight (approximately 12 h).

Once the sulphonation is complete, the reaction mixture is cooled to 90° C. and then poured, still hot, into 250 g of ice. The combined mixture is left stirring; once all the ice has melted, 15 of NaCl are added, precipitating the disulphonated monomer. The precipitate is subsequently filtered off and then dried at 80° C. under vacuum. The dry product is subsequently mixed with 250 ml of distilled water and heated up to 90° C. Once all the product has dissolved, the pH is adjusted to 7.0 by adding 1% NaOH (aqueous). The solution is cooled to ambient temperature; the majority of the product has precipitated at that time. The white product is separated from the aqueous phase by filtration. The product remaining in the aqueous phase is precipitated by adding 15 g of NaCl. The product is filtered off and dried overnight at 150° C. under vacuum. No other purification is necessary.

5.92 g (yield 85%) of monomer B1, of formula:

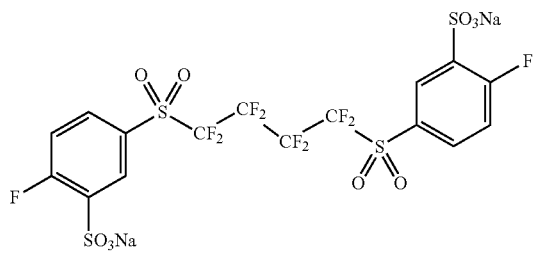

are thus obtained.

The NMR analysis gives the following results:
$^1$H NMR, 500 MHz (d$_6$-DMSO): 7.67-7.70 (m, 2H), 8.20-8.23 (m, 2H), 8.29-8.31 (m, 2H).

Figure 18:
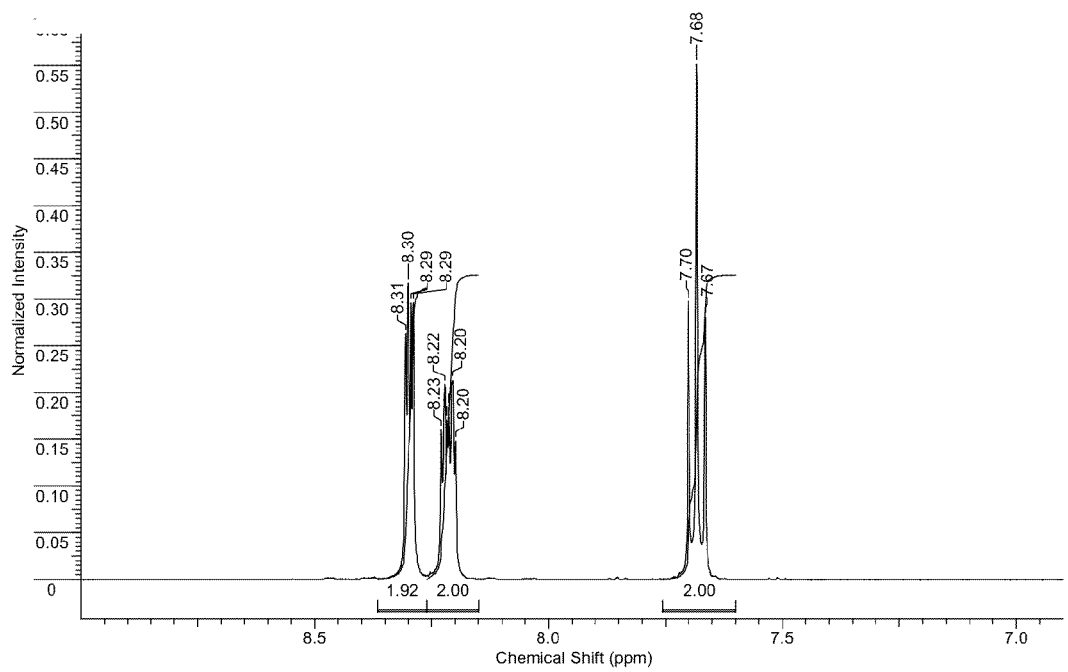

The $^1$H NMR spectrum (500 MHz) of the monomer B1 thus obtained, dissolved in d$_6$-DMSO, is reproduced in FIG. 18.

The product appears pure according to a thin layer chromatography ("TLC") analysis on silica plates using a dichloromethane/ethyl acetate/methanol (7:7:6) mixture.

Finally, the molecular weight of the product, as measured by "ESI" (Electrospray Ionization) mass spectrometry (negative mode (M$^-$-Na$^+$); water/acetone 1/1 mixture) is equal to 698.8 (calculated theoretical value equal to 699.5).

V-3. Synthesis of the Monomer B8

The monomer B8, to recapitulate, not in accordance with the present invention, is disulphonated 1,4-bis(4-fluorobenzophenone)perfluorobutane, the formula of which is as follows:

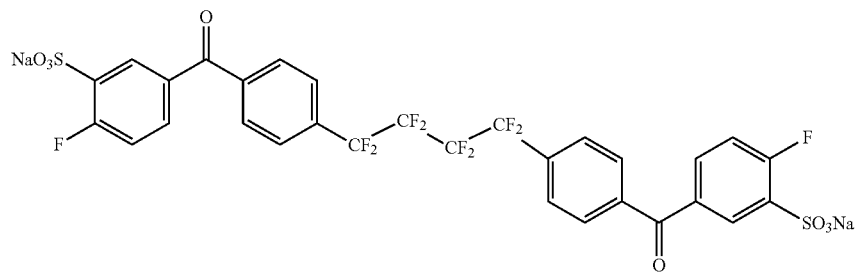

This monomer B8 (or Compound 9) was prepared according to the procedure represented diagrammatically in FIG. 19, in three successive stages, as described in detail below.

V-3-A) Stage 1

Figure 19A:
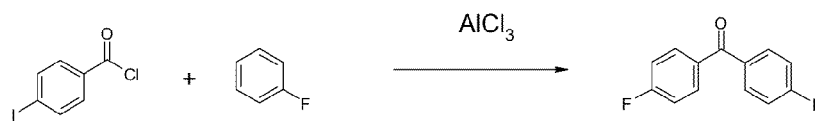

During a first stage, the Compound 7 or 4-iodo-4'-fluorobenzophenone is prepared in accordance with FIG. 19A.

4-Iodobenzoyl chloride (30 g, i.e., 112.6 mmol), aluminium chloride (15.0 g, i.e., 112.7 mmol) and fluorobenzene (21.7 g, i.e., 225.8 mmol) are added to a predried 250 ml round-bottomed flask. The mixture is stirred at ambient temperature under a gentle stream of nitrogen overnight. The following day, a solid has appeared and stirring is no longer possible. An additional 20 ml of fluorobenzene are then added and the reactants are mixed at 40° C. (temperature inside the round-bottomed flask) for 3 h. The apparatus is placed at 40° C. under vacuum (water pump) and the excess fluorobenzene is distilled off (for 30 min).

200 g of ice are directly added to the round-bottomed reaction flask, followed immediately by 60 ml of 37% HCl. The solid product thus obtained is reduced to a powder in a ceramic mortar, then stirred in water until a white powder is obtained, finally separated from the HCl solution by filtration (filter paper) and washed until a neutral pH is obtained. The solid is dried at ambient temperature (23° C.) using the water pump, then mixed with 200 ml of ethanol and finally heated at 60° C. (temperature inside the round-bottomed flask) until everything is dissolved. The compound is finally precipitated by cooling the ethanol at ambient temperature.

The final product (approximately 30 g) is purified by silica (300 g) chromatography using a hexane/ethyl acetate mixture (ratio by weight 16/4) as mobile phase. The product is separated from the mobile phase on a rotary evaporator and dried at 80° C. overnight (under vacuum). The final cream-coloured product (25 g) proves to be pure by NMR analysis and TLC chromatography in the hexane/ethyl acetate (ratio 16/4) mixture, with a melting point (measured by DSC) of approximately 137° C.

The Compound 7, of formula:

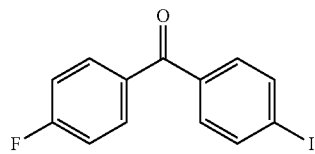 [SMILES: O=C(c1ccc(F)cc1)c1ccc(I)cc1]

is thus obtained.

The NMR analysis gives the following results:
$^1$H NMR, 500 MHz (CD$_2$Cl$_2$): 7.17-7.20 (m, 2H), 7.48-7.50 (m, 2H), 7.80-7.82 (m, 2H), 7.87-7.89 (m, 2H).

V-3-B) Stage 2

Figure 19B:
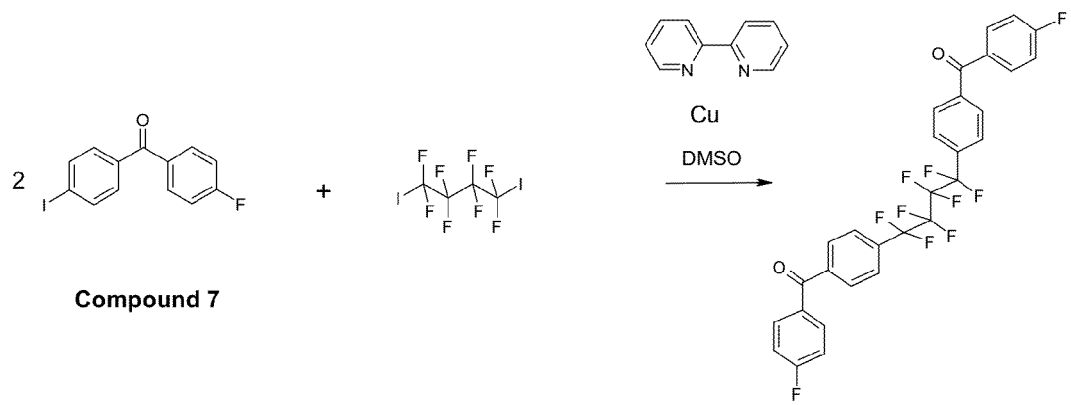

Then, during a second stage, the Compound 8 or 1,4-bis (4-fluorobenzo-phenone)perfluorobutane is prepared according to the procedure which follows and which is represented diagrammatically in FIG. 19B.

17.0 g of 4-iodo-4'-fluorobenzophenone (i.e., 52.13 mmol), 2.0 g of 2,2'-bipyridyl (i.e., 12.83 mmol), followed by 11.83 g of 1,4-diiodoperfluorobutane (i.e., 26.06 mmol) and 150 ml of anhydrous DMSO, are introduced into a predried 500 ml four-necked round-bottomed flask. Subsequently, 6.60 g of copper powder are added and the solution is heated at 65° C. (the oil bath is regulated at 74° C.) for 5 h under a nitrogen stream with continual stirring.

The reaction mixture is cooled to ambient temperature and then poured into 500 ml of cold water; the product precipitates and then it is filtered off and dissolved with 1 liter of dichloromethane. The organic phase is subsequently dried with anhydrous $Na_2SO_4$. The final product is purified by silica (300 g) chromatography in a dichloromethane/cyclohexane (1/1) mixture.

The Compound 8 in the form of a white powder, of formula:

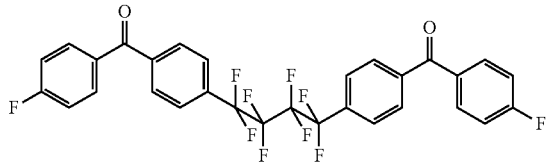 [SMILES: O=C(c1ccc(F)cc1)c1ccc(C(F)(F)C(F)(F)C(F)(F)C(F)(F)c2ccc(C(=O)c3ccc(F)cc3)cc2)cc1]

is thus obtained.

The NMR analysis gives the following results:

$^1$H NMR, 500 MHz ($CD_2Cl_2$): 7.19-7.23 (m, 2H), 7.73-7.75 (d, 4H), 7.83-7.87 (m, 8H).

$^{19}$F NMR, 471.3 MHz ($CDCl_3$): 105.04 (m, 2F), 111.44-111.50 (d, 4F), 121.49-121.55 (m, 4F).

The melting point of the product (measured by DSC) is equal to approximately 222° C.

V-3-C) Stage 3

Figure 19C:
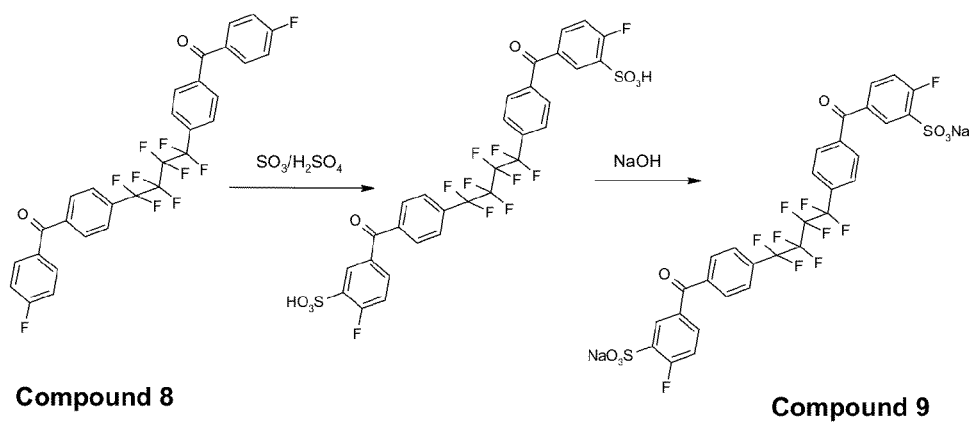

Finally, during a third and final stage, the Compound 9 or disulphonated 1,4-bis(4-fluoro-benzophenone)perfluorobutane is prepared according to the procedure which follows and which is represented diagrammatically in FIG. 19C.

The Compound 8 (2.5 g, i.e., 4.18 mmol) is placed in a 50 ml four-necked round-bottomed flask dried beforehand using a hot-air gun and placed under a stream of nitrogen. 6 g of sulphuric acid (distilled twice, Sigma-Aldrich) and 10 g of oleum (65%, Merck) are added directly to the solid. The reaction medium immediately becomes dark. The exiting gaseous products are purged in an empty glass trap, followed by a trap filled with 30% NaOH. The reaction medium is heated at approximately 130° C. (approximately 138° C. in the oil bath) for 4 h under a moderate stream of nitrogen moving above the solution.

Once the sulphonation is complete, the reaction mixture is allowed to cool to ambient temperature and then it is poured into 63 g of ice and left stirring. Once all the ice has melted, 6.25 g of NaCl are added. The solution is heated at 100° C. and then cooled to ambient temperature in order for the sulphonated monomer to precipitate. The precipitate is subsequently again dissolved in 15 ml of water and again heated at 100° C. in order to convert it back into the liquid form. Once all the product has dissolved, the pH is adjusted to 7.0 by adding 10% NaOH (aq.) dropwise. The solution is allowed to cool to ambient temperature. The cream white solid thus obtained is separated from the aqueous phase by filtration. The product is dried at 150° C. overnight (under vacuum).

The Compound 9 (monomer B8), of formula:

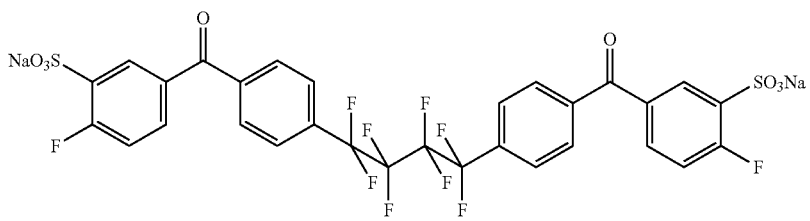

is thus obtained.

Figure 20:
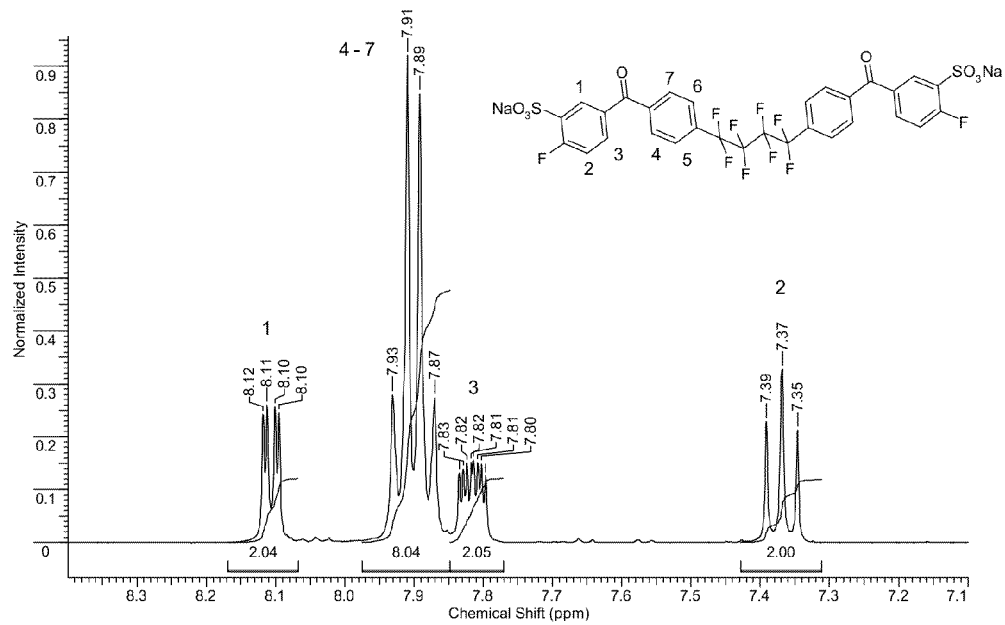

The $^1$H NMR spectrum (500 MHz) of the monomer B8 thus obtained, dissolved in $d_6$-DMSO, is reproduced in FIG. 20.

The NMR analysis gives the following results:

$^1$H NMR, 500 MHz ($d_6$-DMSO): 7.35-7.39 (m, 2H), 7.80-7.83 (m, 2H), 7.87-7.93 (m, 8H), 8.09-8.10 (d, 1H), 8.11-8.12 (d, 1H).

Finally, the molecular weight of the product, as measured by "ESI" (Electrospray Ionization) mass spectrometry (negative mode; water/acetone 1/1 mixture), is equal to 778.9 (calculated theoretical value equal to 779.6).

V-4. Synthesis of the Polymer 1

Figure 21:
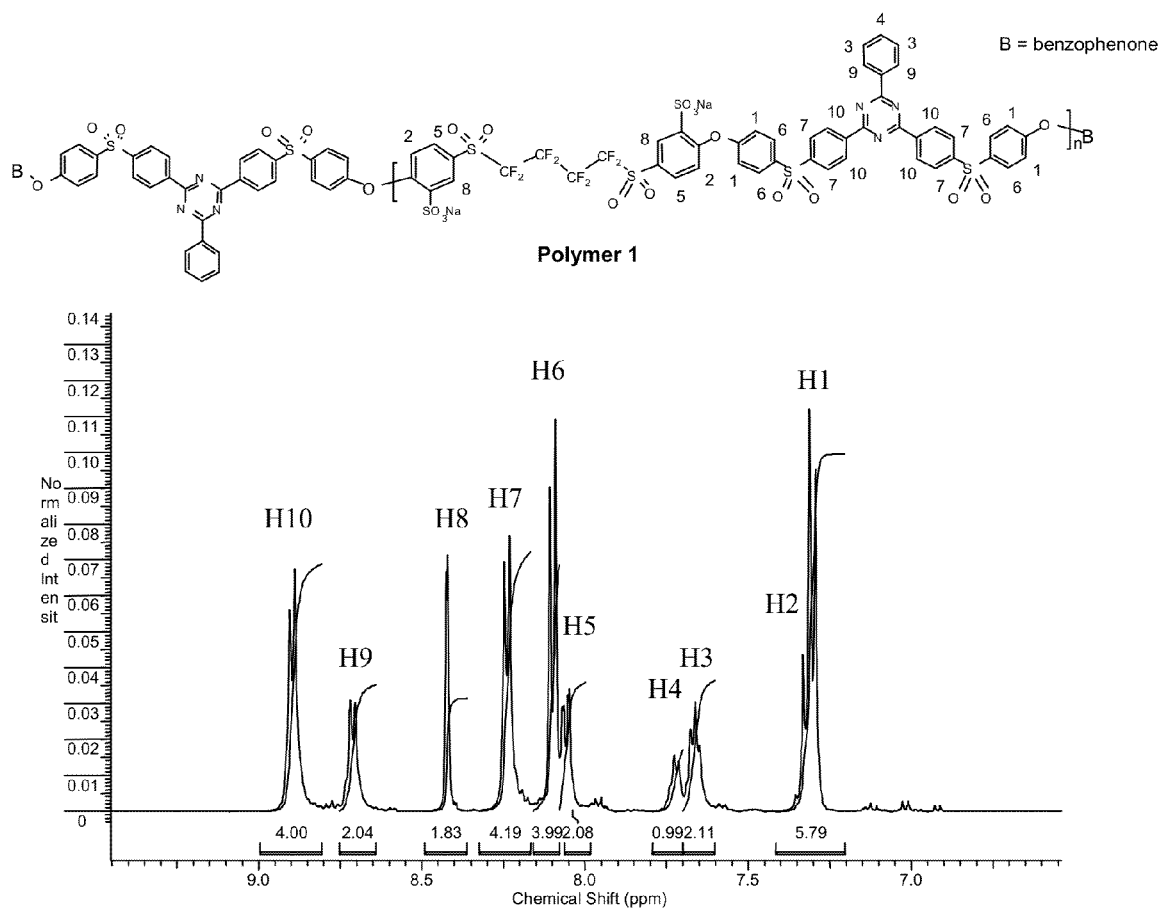

This example describes, in a detailed manner, the synthesis, from the monomers A1 (in accordance with the invention) and B1 (not in accordance with the invention) described above, of the Polymer 1 in the sulphonated form, blocked by benzophenone groups, as represented in FIG. 21.

The monomer A1 is dried at 60° C. under vacuum overnight. The monomer B1 and $Na_2CO_3$ are dried separately at 150° C. under vacuum overnight. The three compounds are then mixed and dried at 160° C. under vacuum for one hour. The copolymerization of monomers A1 and B1 takes place in a 100 ml three-necked round-bottomed flask. The round-bottomed flask is equipped with a nitrogen inlet, a thermometer, a magnetic stirrer and a Dean & Stark separator surmounted by a reflux condenser. The glass parts of the apparatus are dried under vacuum using a hot-air gun in order to reach a temperature of at least 100° C. in the round-bottomed reaction flask.

The round-bottomed reaction flask is charged with the monomer A1 (1.89 g, i.e., 3.04 mmol or 1 eq.), the monomer B1 (2.20 g, i.e., 3.04 mmol or 1 eq.), the anhydrous sodium carbonate (0.97 g, i.e., 9.13 mmol or 3 eq.), anhydrous N,N-dimethylacetamide (20 ml) and toluene (4.0 ml, azeotropic agent). The round-bottomed reaction flask is heated at 100° C. in an oil bath for one hour (azeotropic distillation). The valve for circulation of the toluene is subsequently closed and the toluene is distilled off at 100° C. The temperature of the oil bath is subsequently increased to approximately 148° C. and the residual toluene is removed by distillation for an additional 60 min, so that all the toluene is removed from the reaction and so that the temperature increases to 140° C. inside the round-bottomed flask. The toluene is emptied from the Dean & Stark separator and the temperature of the oil bath is increased to approximately 159° C. and maintained at this value overnight. After approximately 20 h, the temperature of the oil bath is increased to approximately 168° C. (approximately 152° C. inside the round-bottomed flask) and the polymerization continues for 4 hours. The temperature of the reaction is brought down to approximately 130° C. inside the round-bottomed flask by removing the round-bottomed flask from the oil bath. 8 mg of 4-fluorobenzophenone dissolved in 5 ml of anhydrous N,N-dimethylacetamide are subsequently added to the reaction using a syringe. The round-bottomed flask is placed back in the oil bath and the reaction continues at approximately 152° C. (168° C. in the oil bath) for a period of an additional 4 h. The reaction mixture is allowed to cool to ambient temperature and the polymer is subsequently poured into 500 ml of isopropanol. The fibrous precipitate is recovered by filtration and washed with isopropanol and with water until a neutral pH is obtained (washing out of the residual salts). The product is subsequently dried at 60° C. under vacuum overnight. Purification is carried out by precipitation of the polymer, dissolved in N,N-dimethylacetamide, poured dropwise into diethyl ether with continual stirring.

The formula of the Polymer 1 thus obtained, in the sulphonated and benzophenone-blocked form, is represented in FIG. 21, along with its $^1$H NMR spectrum (500 MHz), dissolved in $d_6$-DMSO.

V-5. Synthesis of the Polymer 7

Figure 22:
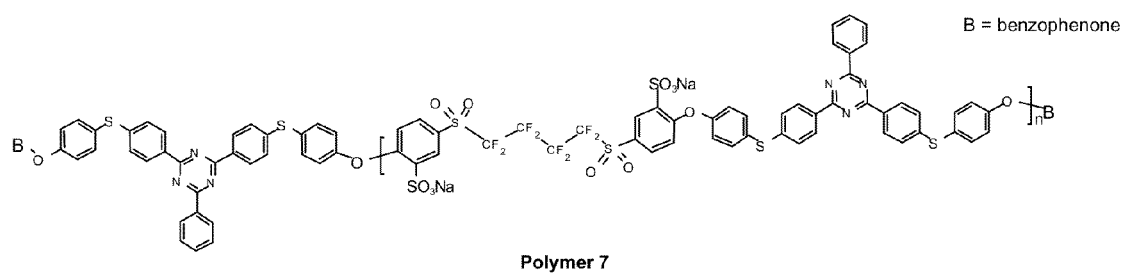
Figure 22:
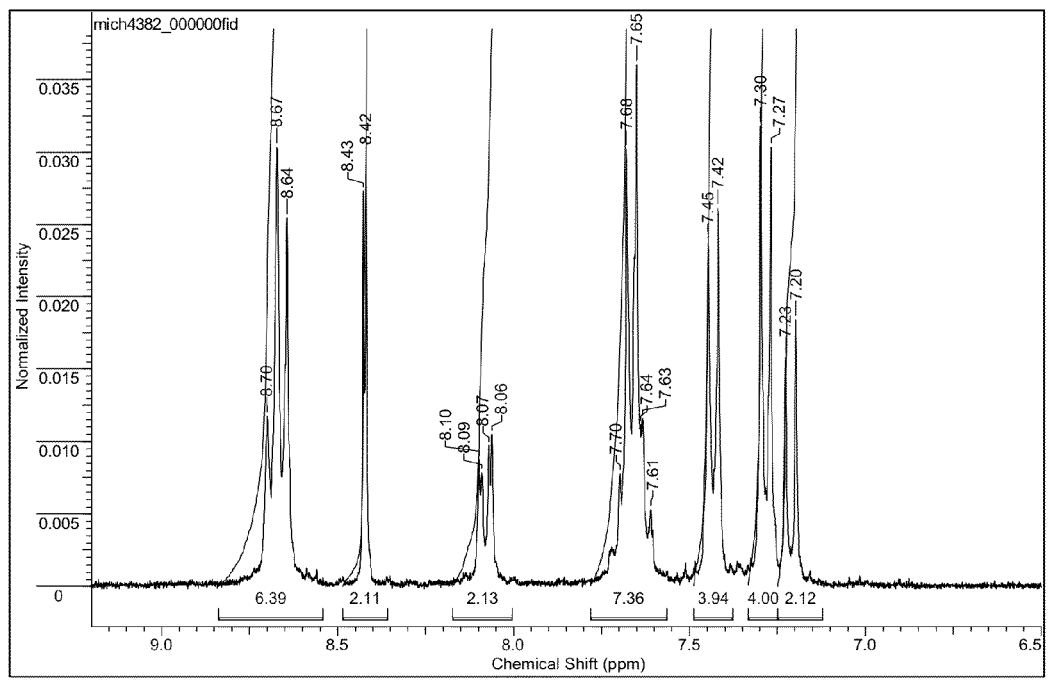

This example describes in a detailed way the synthesis of the Polymer 7, according to a process already commented on in FIG. 13, from the Compound 2 (in accordance with the invention) and the Compound 6 (not in accordance with the invention) described above, this Polymer 7 being obtained here, on the one hand, in the sulphonated form and, on the other hand, in the form blocked by benzophenone groups, as represented in FIG. 22.

The monomer denoted A7 or A4 (Compound 2) is dried at 80° C. under vacuum overnight. The monomer denoted B7 or B1 (Compound 6) and Na$_2$CO$_3$ are dried separately at 150° C., mixed and then the combined mixture is dried at 160° C. under vacuum for one hour. The copolymerization of the monomers A7 and B7 is carried out in a 100 ml three-necked round-bottomed flask. The round-bottomed flask is equipped with a nitrogen inlet, a thermometer, a magnetic stirrer and a Dean & Stark separator surmounted by a reflux condenser. The glass parts of the apparatus are dried under vacuum.

For a 50 mol % disulphonation, the round-bottomed flask is charged with the monomer A7 (1.695 g, i.e., 3.04 mmol or 1 eq.), the monomer B7 (2.196 g, i.e., 3.04 mmol or 1 eq.), the anhydrous sodium carbonate (0.968 g, 9.13 mmol, 3 eq.), anhydrous N,N-dimethylacetamide (20 ml) and toluene (4.0 ml, azeotropic agent). The round-bottomed reaction flask is heated at 100° C. in an oil bath for two hours (azeotropic distillation). The valve for circulation of the toluene is subsequently closed and the toluene is distilled off at 100° C. The temperature of the oil bath is subsequently increased to 148° C. and the residual toluene is removed by distillation for an additional one hour, so that all the toluene is removed from the reaction and so that the temperature reaches 140° C. inside the round-bottomed flask. The toluene is emptied from the Dean & Stark separator and the temperature of the oil bath is increased to 159° C. and then maintained at this value overnight.

After approximately 20 h, the round-bottomed flask is removed from the oil bath and allowed to cool down to approximately 130° C. inside the round-bottomed reaction flask. 8 mg of 4-fluorobenzophenone are then dissolved in 5 ml of anhydrous N,N-dimethylacetamide and the solution is added to the reaction using a syringe. The round-bottomed flask is placed back in the oil bath and the reaction continues at approximately 145° C. (approximately 158° C. in the oil bath) for an additional 4 h. The reaction mixture is allowed to cool to ambient temperature; the product obtained is subsequently poured into 200 ml of 2-propanol (isopropanol). The fibrous precipitate is recovered by filtration.

The polymer is then dried under vacuum at 80° C. overnight. The sodium carbonate is extracted from the polymer by immersing the latter in 50 ml of distilled water with stirring with a magnetic bar for 30 min. The pH of the solution is adjusted down to 7 by dropwise addition of 10% HCl (aq.). The polymer is subsequently dried at 80° C. under vacuum (approximately 12 hours).

The formula of the Polymer 7 thus obtained, in the sulphonated and benzophenone-blocked form, is represented in FIG. 22, along with its $^1$H NMR spectrum (500 MHz), dissolved in $d_6$-DMSO.

V-6. Synthesis of the Polymer 8

This example describes in a detailed way the synthesis of the Polymer 8, according to a process already commented on in FIG. 14, from the monomer A8 (or Compound 2 in accordance with the invention) and the monomer B8 (or Compound 9 not in accordance with the invention) described above, this Polymer 8 being obtained here, on the one hand, in the sulphonated form and, on the other hand, in the form blocked by benzophenone groups.

The monomer B8 and Na$_2$CO$_3$ are first of all dried separately at 150° C. overnight (under vacuum) and then they are mixed together at 160° C. for 1 h. The monomer A8 is itself also dried at 80° C. (under vacuum) overnight.

The polymerization is carried out in a 100 ml three-necked round-bottomed flask. The round-bottomed flask is surmounted by a nitrogen inlet, a thermometer, a stirrer and a Dean & Stark separator surmounted by a reflux condenser. The glass parts of the apparatus (including the reflux condenser and the Dean & Stark separator) are dried under vacuum using a hot-air gun. The round-bottomed flask is charged with the monomer A8 (0.848 g, i.e., 1.52 mmol), the monomer B8 (1.22 g, i.e., 1.52 mmol), the anhydrous sodium carbonate (0.48 g, i.e., 4.57 mmol; three times the excess), dry N,N-dimethylacetamide DMA (20 ml) and toluene (4 ml; azeotropic agent). The round-bottomed reaction flask is heated in an oil bath at 100° C. The temperature of the oil bath is subsequently increased to approximately 148° C. and the residual toluene is distilled off (140° C. inside the round-bottomed reaction flask).

The trap of the Dean & Stark separator is emptied (toluene drained off) and the temperature of the oil bath is increased to approximately 159° C. (approximately 150° C. inside the round-bottomed flask) and is then maintained at this temperature for approximately 20 hours.

The temperature of the reaction is then lowered to 100° C. inside (the round-bottomed flask is raised above the oil bath) and then 4 mg of 4-fluorobenzophenone dissolved in 5 ml of DMA are injected into the reaction using a syringe. The blocking reaction is subsequently continued in an oil bath regulated at approximately 145° C. (internal temperature) for 4 h. The reaction mixture is allowed to cool to ambient temperature and then the polymer is poured into 300 ml of isopropanol. The fibrous precipitate is recovered by filtration and dried in an oven at 80° C. overnight (under vacuum). The sodium carbonate is removed from the polymer by washing in 30 ml of water and acidified by dropwise addition of 10% HCl down to pH 7. The final polymer thus obtained is dried at 100° C. under vacuum.

The NMR analysis gives the following results:
$^1$H NMR (500 MHz) $d_6$-DMSO: 7.08-7.09 (d, 2H), 7.17-7.19 (d, 4H), 7.39-7.40 (d, 4H), 7.62-7.64 (m, 6H), 7.80-7.82 (d, 2H), 7.79-7.85 (m, 8H), 8.27-8.28 (s, 2H), 8.65-8.66 (d, 4H),), 8.69-8.70 (d, 2H).

V-7. Manufacture of PEM Membranes

In this test, Polymer 1, Polymer 2 and Polymer 8 membranes are prepared according to the "solvent casting" technique as described below.

The polymer (625 mg), dissolved beforehand in 8 ml of N,N-dimethylacetamide, is filtered through a PTFE (polytetrafluoroethylene) microfilter ("Millipore") having a pore size of approximately 0.45 μm. The polymer solution thus filtered is then run into a mould consisting of two superimposed glass sheets, the upper sheet comprising a recess (dimensions 9 cm×9 cm) with a depth equal to 1 mm; the solution is subsequently heated at 50° C. for 24 h and then at 60° C. for 2 h. The traces of organic solvent are then removed from the membrane thus formed by immersing the latter in a bath of distilled water for approximately 12 h.

After final drying at 60° C. under vacuum for 2 h, a strong and transparent membrane, with a thickness which is equal to approximately 50 μm, is thus obtained, which is ready for characterization.

V-8. Characterization of the PEM Membranes

V-8-A) Proton Conductivity

For the acidification of the membrane (to remind, exchange of the $M^+$ cation by $H^+$), the Polymers 1, 2 and 8 are initially immersed in 200 ml of $H_2SO_4$ (aq.), respectively 3.8M (for the Polymer 1) and 1.9M (for the Polymers 2 and 8), for 2 h. Use is made of the acid $H_2SO_4$ distilled twice (Sigma Aldrich), in order to avoid traces of metals. Distilled water is subsequently added in several stages (total duration approximately 12 h) in order to reach a pH equal to 7; the membrane is subsequently thus stored in the distilled water overnight (approximately 12 hours).

The proton conductivity of the membrane, expressed in S/cm (Siemens per centimeter) is determined as indicated below.

Membranes in the form of discs with a diameter of 2 cm (thickness 50 μm) are cut out using a hollow punch. The proton conductivity of the membrane is determined by measuring the real part (Ohmic) and the imaginary part (Capacitance) of the complex impedance, within the range of frequencies lying between 100 kHz and 10 Hz (with amplitude of 100 mV AC). The measurements are carried out with an impedance/AC potentiostat (Zahner, Germany). Nyquist graphs are generated by the measurements of a successive stack of one, two, three and up to six membranes (completely humidified) sandwiched between two platinum electrodes having the same circular shape as the membranes.

For each measurement, the value intercepting the real axis of the Nyquist graph is given, that is to say a value of the imaginary component of the impedance at zero. In general, these points are aligned on an affine straight line, the slope of which directly determines the value of the resistance of the membrane. Its ordinate at the origin determines the contact resistance between the membranes and the platinum electrodes. The latter values and the knowledge of the thickness make it possible to calculate in a known way the resistivity of the membrane; the inverse of this value is the conductivity.

Thus tested, the membranes resulting from the Polymer 1, Polymer 2 and Polymer 8 have shown noteworthy proton conductivity values respectively equal to 89 mS/cm, 73 mS/cm and 35 mS/cm at 25° C. (100% humidity), of the same order of magnitude as, indeed even better than, the conductivity value (approximately 70 mS/cm) measured on the commercial membrane ("Nafion® 112") with the same thickness and rigorously tested under the same conditions.

V-8-B) Water Absorption Capacity and Dimensional Stability

Once the membrane has been acidified, it is dried at 100° C. under vacuum for 2 hours. Its weight is immediately measured, before it captures atmospheric moisture. The membrane samples are then immersed in distilled water at ambient temperature until saturated (at this stage, no additional weight gain due to water is then observed).

The water absorption capacity, expressed in %, is calculated as the difference between the weight of the wet membrane and the weight of the dry membrane. The dimensional stability, also expressed in %, is the ratio of the main dimension of the dry membrane to the main dimension of the completely humidified membrane.

It is noted that the membranes of the Polymer 1, Polymer 2 and Polymer 8 have a water absorption capacity respectively equal to 27%, 17% and 20% of their weight, in comparison with a value of approximately 23% for the commercial membrane ("Nafion® 112"). Their dimensional stability is respectively equal to 20%, 5% and 1%, in comparison with a value of 7% for the control commercial membrane.

In other words, it is found that these membranes resulting from the monomers in accordance with the invention unexpectedly exhibit not only a reduced water absorption capacity but also a noteworthy dimensional stability, so many factors which are determining for the endurance and the chemical stability of the membrane while operating in a PEM fuel cell.

V-8-C) Surface Morphology

Horizontal and transverse membrane cross sections are produced (each sample with a thickness of approximately 70 nm) and are then coated in a liquid epoxy resin. The resin is then polymerized at 60° C. for 48 h in the presence of a curing agent and an accelerator.

After impregnating the membrane samples in an aqueous solution of uranyl acetate ($UO^{2+}(CH_3COO^-)_2$) and then of lead citrate, the morphology of the membrane is observed using a transmission electron microscope (Philips TEM CM100; magnification 245 000).

The electron microscopy photographs, respectively recorded on a horizontal cross section (FIG. 23A) and on a transverse cross section (FIG. 23B) of a membrane in accordance with the invention (Polymer 1), are reproduced in FIG. 23.

A mean pore size equal to 2.4 nm with a standard deviation of 0.5 nm constitutes a particularly noteworthy and unexpected result for a person skilled in the art. In comparison with the known commercial membranes, the invention thus makes it possible to obtain a greatly improved surface morphology with, on the one hand, very substantially reduced pore sizes and, on the other hand, a particularly narrow distribution in the sizes; such characteristics are determining for the overall electrical performance of the membrane, for its properties of impermeability to gases and for its final endurance.

V-8-D) Performance in a PEM Fuel Cell

The performances of the membranes can be tested on a test bed for fuel cells on which the temperature, the pressure, the flow rate and the humidity of the gases can be regulated. The gases used are pure hydrogen and pure oxygen, at a temperature of 65° C.

The fuel cell used in these tests is composed of a single cell comprising the polymer membrane to be tested, positioned between two "GDE" (Gas-Diffusion Electrode) layers, two graphite bipolar plates and two standard electrodes ("ELE 0107" from Johnson Matthey) having a platinum content of approximately 0.4 mg/cm².

The membrane to be tested is first of all dried between two nonwovens (sterile chamber grade, "Sontara Micropure 100"—supplier DuPont). It is subsequently pressed between two glass plates at 60° C. for 3 h. The MEA assembly is obtained by hot pressing a Pt/C catalysis layer positioned on each side of the membrane (115° C., 125 MPa). At this stage, the MEA assembly can be assembled between two bipolar plates to form a single cell of a fuel cell which is ready to operate when it is fed with hydrogen and oxygen.

For the requirements of the test, the fuel cell is subjected to stationary conditions (0.7 V) or to shutdown and startup or "OCV" (Open Circuit Voltage) situations, in order, in a known way, to subject the membrane to the most aggressive operating conditions (e.g., peroxides, free radicals, and the like) and to finally deduce therefrom its overall chemical resistance.

FIG. 24 reproduces the "polarization" curve, the voltage of the single cell being recorded as a function of the current density delivered by the fuel cell, on the one hand for the membrane consisting of the Polymer 1 (curve $C_A$) and, on the other hand, for the commercial membrane ("Nafion® 112" polymer, curve $C_B$).

The following comments result from the reading of these two curves:
  first of all, at high voltage and zero current (open electrical circuit), it is noted that the polarization voltage is equivalent for the two membranes, which illustrates, to a person skilled in the art, an equivalent permeability to the gases ($O_2$ and $H_2$);
  subsequently, a substantially identical slope of the two curves is observed in their central linear part (typically between 200 and 1200 mA/cm²), which testifies to an identical electrical performance of the two membranes, without even a particular optimization of the electrodes (anode and cathode) for the specific membrane of the invention;
  finally, at high current and low voltage (typically above 1200 mA/cm²), it is observed that the behaviour of the two membranes remains similar, which confirms a very good proton conductivity of the membrane at high current.

In conclusion, the monomers of the invention make it possible to manufacture polymers and PEM membranes which, unexpectedly, exhibit a chemical and dimensional stability and an ion conductivity which are at least equivalent, if not superior, to those of the commercial membranes of the Nafion® type which have, however, been developed for a very long time; these polymers additionally exhibit a noteworthy chemical stability and a noteworthy resistance to oxidation in comparison with the triazine polymers of the prior art.

In addition, compared with the triazine monomers of the prior art, the monomers of the invention are relatively inexpensive and are capable of being employed according to simple, economical and environmentally friendly processes of synthesis.

The invention claimed is:

1. A sulphur-containing triazine monomer corresponding to a formula (I):

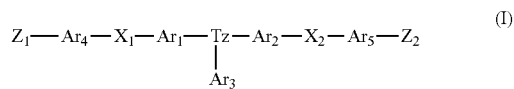

in which:
  Tz represents a 1,3,5-triazine nucleus;
  $X_1$ and $X_2$, which are identical or different, represent S, SO, or $SO_2$;
  $Ar_1$, $Ar_2$, $Ar_4$ and $Ar_5$, which are identical or different, represent a substituted or unsubstituted phenylene group;
  $Ar_3$ represents a substituted or unsubstituted phenyl group;
  $Z_1$ and $Z_2$, which are identical or different, are selected from a group that includes halogens, hydroxyl, alkoxyls, thiol, carboxyls, carboxylates, amino, sulphonamido, acyl chloride, sulphonyl chloride, sulphonyl fluoride, isocyanate, and combinations thereof.

2. The triazine monomer according to claim 1, wherein $Z_1$ and $Z_2$, which are identical or different, are selected from a group that includes halogens, hydroxyl, thiol, and combinations thereof.

3. The triazine monomer according to claim 2, wherein the triazine monomer corresponds to a formula (II):

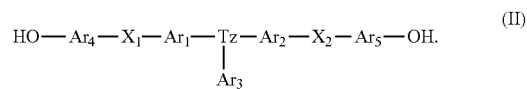

4. The triazine monomer according to claim 2, wherein $Z_1$ and $Z_2$, which are identical or different, are halogens.

5. The triazine monomer according to claim 4, wherein the triazine monomer corresponds to a formula (III):

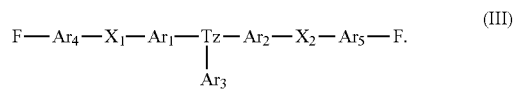

6. The triazine monomer according to claim 4, wherein the triazine monomer corresponds to a formula (IV):

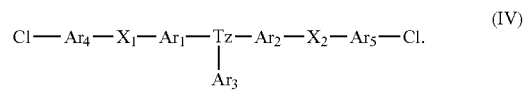

7. The triazine monomer according to claim 1, wherein the triazine monomer is a suphonated monomer that includes a sulphonic (—$SO_3H$) group or a sulphonate (—$SO_3M$) group, in which M represents an alkali metal cation.

8. The triazine monomer according to claim 7, wherein the sulphonic (—$SO_3H$) group or the sulphonate (—$SO_3M$) group is carried by a phenyl group or a phenylene group or by at a substituent thereof.

9. A process for synthesizing a triazine polymer, comprising:
performing polycondensation of a triazine monomer corresponding to a formula (I):

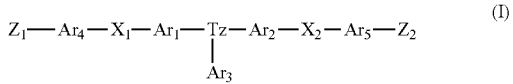

in which:
Tz represents a 1,3,5-triazine nucleus;
$X_1$ and $X_2$, which are identical or different, represent S, SO, or $SO_2$;
$Ar_1$, $Ar_2$, $Ar_4$ and $Ar_5$, which are identical or different, represent a substituted or unsubstituted phenylene group;
$Ar_a$ represents a substituted or unsubstituted phenyl group;
$Z_1$ and $Z_2$, which are identical or different, are selected from a group that includes halogens, hydroxyl, alkoxyls, thiol, carboxyls, carboxylates, amino, sulphonamido, acyl chloride, sulphonyl chloride, sulphonyl fluoride, isocyanate, and combinations thereof.

10. A method of manufacturing a PEM-type fuel cell, comprising:
using a triazine monomer or produce a polymer membrane used in the PEM-type fuel cell, wherein the triazine monomer corresponds to a formula (I):

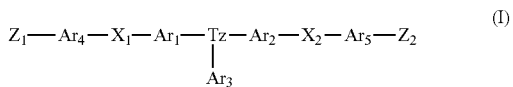

in which:
Tz represents a 1,3,5-triazine nucleus;
$X_1$ and $X_2$, which are identical or different, represent S, SO, or $SO_2$;
$Ar_1$, $Ar_2$, $Ar_4$ and $Ar_5$, which are identical or different, represent a substituted or unsubstituted phenylene group;
$Ar_a$ represents a substituted or unsubstituted phenyl group;
$Z_1$ and $Z_2$, which are identical or different, are selected from a group that includes halogens, hydroxyl, alkoxyls, thiol, carboxyls, carboxylates, amino, sulphonamido, acyl chloride, sulphonyl chloride, sulphonyl fluoride, isocyanate, and combinations thereof.

* * * * *